(12) United States Patent
Bornhoft et al.

(10) Patent No.: US 9,682,243 B2
(45) Date of Patent: Jun. 20, 2017

(54) BATTERY CHARGING TERMINATION PARAMETER BASED ON PREVIOUS CHARGING SESSION DURATION

(75) Inventors: Reid K. Bornhoft, Lino Lakes, MN (US); Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 835 days.

(21) Appl. No.: 13/360,531

(22) Filed: Jan. 27, 2012

(65) Prior Publication Data

US 2013/0193931 A1 Aug. 1, 2013

(51) Int. Cl.
*H02J 7/00* (2006.01)
*A61N 1/378* (2006.01)
*H02J 7/02* (2016.01)
*H02J 7/04* (2006.01)
*H02J 17/00* (2006.01)

(52) U.S. Cl.
CPC ............ *A61N 1/3787* (2013.01); *H02J 7/025* (2013.01); *H02J 7/041* (2013.01); *H02J 7/045* (2013.01); *H02J 17/00* (2013.01)

(58) Field of Classification Search
CPC ........... H02J 7/008; H02J 7/0077; H02J 7/045
USPC ......................... 320/155, 157, 158
See application file for complete search history.

(56) References Cited

U.S. PATENT DOCUMENTS

| | | | |
|---|---|---|---|
| 5,200,689 A | 4/1993 | Interiano et al. | |
| 5,670,863 A | 9/1997 | Broell et al. | |
| 6,031,359 A * | 2/2000 | Michelsen | H02J 7/0077 320/141 |
| 6,160,377 A | 12/2000 | Fujii | |
| 6,515,453 B2 | 2/2003 | Feil et al. | |
| 7,957,921 B2 | 6/2011 | Tang et al. | |
| 2009/0273313 A1* | 11/2009 | Scott et al. | 320/134 |
| 2009/0273318 A1* | 11/2009 | Rondoni | A61N 1/37247 320/149 |
| 2010/0102781 A1* | 4/2010 | Svensson | H02J 7/0083 320/157 |
| 2010/0191490 A1 | 7/2010 | Martens et al. | |
| 2011/0018679 A1* | 1/2011 | Davis | H02J 7/025 340/3.1 |

(Continued)

OTHER PUBLICATIONS

U.S. Appl. No. 13/360,520, filed Jan. 27, 2012, entitled "Battery Charging Top-Off,".

(Continued)

*Primary Examiner* — Richard Isla Rodas
*Assistant Examiner* — Manuel Hernandez
(74) *Attorney, Agent, or Firm* — Shumaker & Sieffert, P.A.

(57) ABSTRACT

This disclosure describes techniques for a method of charging a battery. In an example, the method includes charging the battery during a first charging session until a first charging termination parameter value is reached. The method also includes determining, for a second charging session, a second charging termination parameter value based on a duration of the first charging session, wherein the second charging termination parameter value is different than the first charging termination parameter value. The method also includes charging the battery during the second charging session until the second charging termination parameter value is reached.

40 Claims, 11 Drawing Sheets

(56) References Cited

U.S. PATENT DOCUMENTS

2012/0032648 A1* 2/2012 Ghantous et al. ............ 320/139
2012/0043929 A1* 2/2012 Yazami ........................ 320/107

OTHER PUBLICATIONS

Office Action from U.S. Appl. No. 13/360,520, dated Dec. 4, 2014, 9 pp.
Office Action from U.S. Appl. No. 13/360,520, dated Dec. 4, 2014, 8 pp.
Response to Office Action dated Dec. 4, 2014, from U.S. Appl. No. 13/360,520, dated Mar. 4, 2015, 5 pp.
Response to Office Action mailed Jul. 6, 2015, from U.S. Appl. No. 13/360,520, filed Sep. 8, 2015, 11 pp.
Final Office Action for U.S. Appl. No. 13/360,520, mailed Jul. 6, 2015, 10 pages.
Response to Office Action mailed Dec. 18, 2015, from U.S. Appl. No. 13/360,520, filed Mar. 18, 2016, 12 pp.
Office Action from U.S. Appl. No. 13/360,520, dated Dec. 18, 2015, 12 pp.

* cited by examiner

BATTERY CHARGING TERMINATION PARAMETER BASED ON PREVIOUS CHARGING SESSION DURATION

TECHNICAL FIELD

This disclosure is directed to techniques for charging a battery.

BACKGROUND

Devices often make use of one or more rechargeable or non-rechargeable power sources, such as batteries, to provide operating power to circuitry of the device. During operation, the charge level of a power source drops due to power consumption by the device. The device may provide some indication of remaining charge as the power source drains, e.g., as the battery or batteries drain. A user of the device may utilize the remaining charge indication to determine whether the power source needs to be replaced or recharged. By replacing or recharging the power source before the charge on the power source is fully depleted, the user can ensure that operation of the device will not be interrupted, or otherwise adversely impacted, due to power source depletion.

SUMMARY

In general, this disclosure describes techniques for charging a battery, such as a rechargeable battery in an implantable medical device. For example, techniques of this disclosure include charging a battery during a top-off period, which typically occurs during an end period of a charging session (e.g., as the battery approaches full charge). During charging, an impedance of the battery may increase as the battery reaches full charge. To avoid a corresponding rise in voltage, which may cause the battery to swell, a charging current may be reduced during a top-off period. In this way, the battery may be fully charged without increasing the voltage of the battery in a potentially undesirable way.

Certain techniques of this disclosure relate to charging a battery during a top-off period based on a capacity of the battery and a state of charge of the battery. For example, according to the techniques of this disclosure, a capacity of a battery may be determined based on an amount of charge that is consumed during battery discharge. That is, assuming the battery is at full capacity prior to discharge, the capacity of the battery may be determined based on a difference between the initial, full capacity and an amount of charge that is consumed during discharge. When recharging the battery, the battery state of charge may be monitored relative to the determined capacity of the battery. As the state of charge increases toward the capacity of the battery, a current used to charge the battery may be decreased. That is, according to the aspects of this disclosure, the current used to charge the battery during a top-off period toward the end of a charging session may be decreased based on the state of charge of the battery.

Certain techniques of this disclosure also relate to charging a battery during a top-off period until a predetermined charging termination parameter value is reached. According to aspects of this disclosure, the charging termination parameter value for a current charging session may be determined based on a duration of a previous charging session. Additionally or alternatively, in some examples, the charging termination parameter value for the current charging session may be determined based on an amount of charge that was administered to the battery during the previous charging session, or a combination of both the duration and amount of charge. For example, the techniques of this disclosure include adapting the charging termination parameter value (e.g., lowering or raising the value) based on a duration of the previous charging session and/or an amount of charge that was administered during the previous charging session. In some examples, an impedance of a battery may increase over time, which may require a longer charging session to reach the charging termination parameter value. The techniques of this disclosure may be used to account for changing battery impedance, while also maintaining a target charging time.

In one example, aspects of this disclosure are directed to a method of charging a battery. The method includes charging the battery during a first charging session until a first charging termination parameter value is reached; determining, for a second charging session, a second charging termination parameter value based on a duration of the first charging session, wherein the second charging termination parameter value is different than the first charging termination parameter value; and charging the battery during the second charging session until the second charging termination parameter value is reached.

In another example, aspects of this disclosure are directed to an implantable medical device (IMD) that includes a battery configured to power the IMD; a memory storing instructions; and one or more processors configured to execute the instructions. Upon execution of the instructions, the one or more processors cause charging the battery during a first charging session until a first charging termination parameter value is reached; determining, for a second charging session, a second charging termination parameter value based on a duration of the first charging session, wherein the second charging termination parameter value is different than the first charging termination parameter value; and charging the battery during the second charging session until the second charging termination parameter value is reached.

In another example, aspects of this disclosure are directed to an implantable medical device (IMD) comprising means for charging the battery during a first charging session until a first charging termination parameter value is reached; means for determining, for a second charging session, a second charging termination parameter value based on a duration of the first charging session, wherein the second charging termination parameter value is different than the first charging termination parameter value; and means for charging the battery during the second charging session until the second charging termination parameter value is reached.

The details of one or more aspects of the disclosure are set forth in the accompanying drawings and the description below. Other features, objects, and advantages of the disclosure will be apparent from the description and drawings, and from the claims.

DETAILED DESCRIPTION

Figure 1:
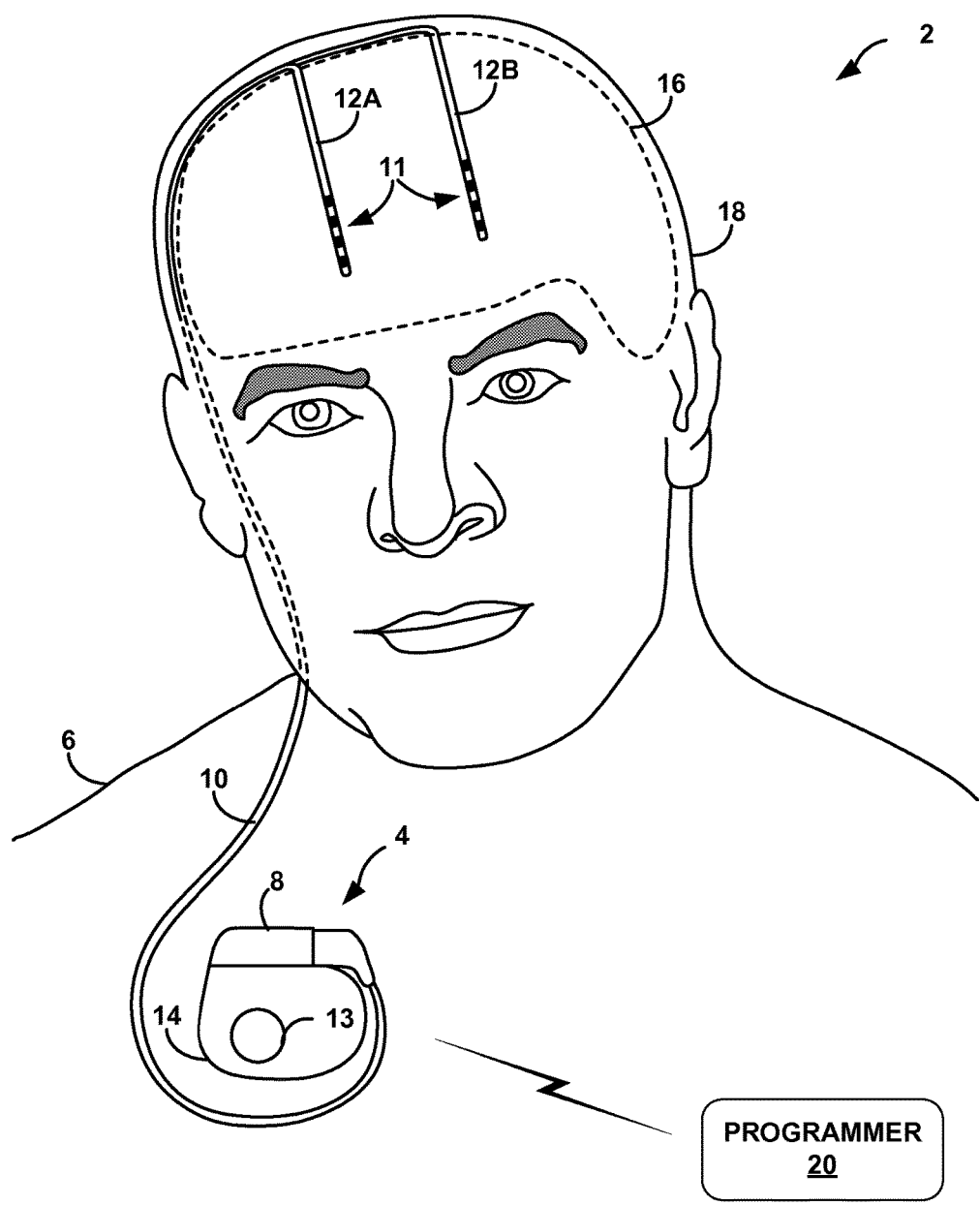
FIG. 1 is a conceptual diagram illustrating an example therapy system that includes an implantable stimulator coupled to a stimulation lead.

In general, this disclosure describes techniques for charging a battery. For example, techniques of this disclosure include charging a battery during a top-off period, which typically occurs during the end of a charging session (e.g., as the battery approaches full charge). That is, during charging, an impedance of the battery may increase as the battery reaches full charge. To avoid a corresponding rise in voltage, which may cause the battery to swell, a charging current may be reduced during a top-off period. In this way, the battery may be fully charged without increasing the voltage of the battery in a potentially adverse way.

Certain techniques of this disclosure relate to charging a battery during a top-off period based on a capacity of the battery and a state of charge of the battery. For example, according to the techniques of this disclosure, a capacity of a battery may be determined based on an amount of charge that is consumed during battery discharge. That is, assuming the battery is at full capacity prior to discharge, the capacity of the battery may be determined based on a difference between the initial, full capacity and an amount of charge that is consumed during discharge. When recharging the battery, the battery state of charge may be monitored relative to the determined capacity of the battery. As the state of charge increases toward the capacity of the battery, a current used to charge the battery may be decreased. That is, according to the aspects of this disclosure, the current used to charge the battery during a top-off period toward the end of a charging session may be decreased based on the state of charge of the battery.

Certain techniques of this disclosure also relate to charging a battery during a top-off period until a charging termination parameter value is reached. The charging termination parameter may include, for example, a minimum charging current cut off value. The minimum charging current cut off value may be a minimum current that is allowed for charging. The charging termination parameter may additionally or alternatively include a power cut off value. For example, a power level cut off value may be approximately equivalent to a minimum power level at which the battery may be charged (e.g., a minimum output power of a programmer or other recharger charging the battery). In still other examples, other charging termination parameters may be used, such as other parameters that indicate when a battery has reached full charge (e.g., battery impedance, and the like).

For example, in an example in which the charging termination parameter is a minimum charging current cut off, a current used to charge the battery may be reduced until a charging current cut off value is reached (e.g., a minimum current that is allowed for charging). According to aspects of this disclosure, the charging current cut off value for a current charging session may be determined based on a duration of a previous charging session and/or amount of charge that was administered to the battery during the previous charging session. For example, the techniques of this disclosure include adapting the charging current cut off value (e.g., lowering or raising the value) based on a duration of the previous charging session and/or an amount of charge that was administered during the previous charging session. In some examples, an impedance of a battery may increase over time, which may require a longer charging session to reach the charging current cut off value. Accordingly, the techniques of this disclosure may allow a charging session to be maintained for a certain duration, while also stopping the charging session prior to the end of the duration if the charging current is too low. While described with respect to a minimum charging current cut off value, it should be understood that other charging termination parameters (e.g., power level, impedance, and the like) may be similarly adjusted according to the techniques of this disclosure.

FIG. 1 is a conceptual diagram illustrating an example system 2 that may be used to deliver stimulation therapy to patient 6, which may implement the techniques of this disclosure. Patient 6 ordinarily, but not necessarily, will be a human. Therapy system 2 includes implantable stimulator 4, which may also be referred to as an implantable medical device (IMD), that delivers electrical stimulation to patient 6 via one or more implantable electrodes, such as electrodes 11 on implantable medical lead 10. The implantable electrodes may be deployed on one or more implantable medical leads, such as implantable medical lead 10, and in some cases on a can electrode. In other examples an implantable stimulator may be a leadless stimulator including electrodes on an external surface of an external housing of the implantable stimulator. Although FIG. 1 shows a fully IMD 4, techniques described in this disclosure may be applied to external stimulators having electrodes deployed via percutaneously implantable leads with a patch electrode or other indifferent electrode attached externally to serve as the can or case. One or more of the electrodes may be located on a housing 14, i.e., "can" or "case," of the IMD 4. In addition, in some cases, implantable electrodes may be deployed on a leadless stimulator.

The electrical stimulation may be in the form of controlled current or voltage pulses or substantially continuous waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs.

In the example illustrated in FIG. 1, IMD 4 is implanted within a subcutaneous pocket in a clavicle region of patient 6. IMD 4 generates programmable electrical stimulation, e.g., a current waveform or current pulses, and delivers the stimulation via an implantable medical lead 10 carrying an array of implantable stimulation electrodes 11. In some cases, multiple implantable leads may be provided. In the example of FIG. 1, a distal end of lead 10 is bifurcated and includes two lead segments 12A and 12B (collectively "lead segments 12"). Lead segments 12A and 12B each include a set of one or more electrodes forming part of the array of electrodes 11. In various examples, lead segments 12A and 12B may each carry four, eight, or sixteen electrodes. In FIG. 1, each lead segment 12A, 12B carries four electrodes, configured as ring electrodes at different axial positions near the distal ends of the lead segments. Throughout the remainder of this disclosure, for purposes of simplicity, the disclosure may generally refer to electrodes carried on "leads" rather than "lead segments."

FIG. 1 further depicts a housing, or can, electrode 13. Housing electrode 13 may be formed integrally with an outer surface of hermetically-sealed housing 14 of IMD 4 or otherwise coupled to housing 14. In one example, housing electrode 13 may be described as an active, non-detachable electrode on the surface of the IMD. In some examples, housing electrode 13 is defined by an uninsulated portion of an outward facing portion of housing 14 of IMD 4. Other divisions between insulated and uninsulated portions of housing 14 may be employed to define two or more housing electrodes, which may be referred to as case or can electrodes. In some examples, housing electrode 13 comprises substantially all of housing 14, or a portion of the housing 14. In other examples, electrode 13 may be formed by an electrode on a dedicated short lead extending from housing 14. As a further alternative, housing electrode 13 could be provided on a proximal portion of one of the leads carrying electrodes 11. The proximal portion may be closely adjacent to housing 14, e.g., at or near a point at which lead 10 is coupled to the housing, such as adjacent to a lead connection header 8 of the housing. In another example, a patch electrode or other indifferent electrode may be attached externally to serve as the can or case.

In some examples, lead 10 may also carry one or more sense electrodes to permit IMD 4 to sense electrical signals from patient 6. Some of the stimulation electrodes may be coupled to function as stimulation electrodes and sense electrodes on a selective basis. In other examples, IMD 4 may be coupled to one or more leads which may or may not be bifurcated. In such examples, the leads may be coupled to IMD 4 via a common lead extension or via separate lead extensions.

A proximal end of lead 10 may be both electrically and mechanically coupled to header 8 on IMD 4 either directly or indirectly via a lead extension. Conductors in the lead body may electrically connect stimulation electrodes located on lead segments 12 to IMD 4. Lead 10 traverses from the implant site of IMD 4 along the neck of patient 6 to cranium 18 of patient 6 to access brain 16. Lead segments 12A and 12B may be implanted within the right and left hemispheres, respectively, in order to deliver electrical stimulation to one more regions of brain 16, which may be selected based on the patient condition or disorder.

IMD 4 may deliver, for example, deep brain stimulation (DBS) or cortical stimulation (CS) therapy to patient 6 via the electrodes carried by, i.e., located on, lead segments 12 to treat any of a variety of neurological disorders or diseases. Example neurological disorders may include depression, dementia, obsessive-compulsive disorder and movement disorders, such as Parkinson's disease, spasticity, epilepsy, and dystonia. DBS also may be useful for treating other patient conditions, such as migraines and obesity. However, the disclosure is not limited to the configuration of lead 10 shown in FIG. 1, or to the delivery of DBS or CS therapy.

Lead segments 12A, 12B are implanted within a desired location of brain 16 through respective holes in cranium 18. Lead segments 12A, 12B may be placed at any location within brain 16 such that the electrodes located on lead segments 12A, 12B are capable of providing electrical stimulation to targeted tissue during treatment.

The electrodes of lead segments 12A, 12B are shown as ring electrodes. Ring electrodes are commonly used in DBS applications because they may be relatively simple to program and are capable of delivering an electrical field to any tissue adjacent to lead segments 12A, 12B. In other implementations, the electrodes of lead segments 12A, 12B may have different configurations. For example, the electrodes of lead segments 12A, 12B may have a complex electrode array geometry that is capable of producing shaped electrical fields.

Therapy system 2 also includes a programmer 20, which may be a clinician or patient programmer. Programmer 20 may be a handheld computing device that permits a user to program stimulation therapy for patient 6 via a user interface, e.g., using input keys and a display. For example, using programmer 20, the clinician may specify stimulation parameters, i.e., create programs, for use in delivery of stimulation therapy. Programmer 20 may support telemetry (e.g., radio frequency (RF) telemetry) with IMD 4 to download programs and, optionally, upload operational or physiological data stored by IMD 4. In this manner, a user, such as the patient or the clinician, may periodically interrogate IMD 4 to evaluate efficacy and, if necessary, modify the programs or create new programs. In some examples, clinician programmer transmits programs to patient programmer in addition to or instead of IMD 4. A clinician programmer may be used more extensively in programming and downloading therapy, and may have more capabilities, such as, for example, the ability to change more therapy parameters than a patient programmer.

A patient programmer may be a handheld computing device, and may include a display and input keys to allow patient 6 to interact with patient programmer and IMD 4. In this manner, patient programmer provides patient 6 with a user interface for control of the stimulation therapy delivered by IMD 4. For example, patient 6 may use patient programmer to start, stop or adjust electrical stimulation therapy. In particular, patient programmer may permit patient 6 to adjust stimulation parameters of a program such as electrode combination, electrode polarities, duration, current or voltage amplitude, pulse width and pulse rate. Patient 6 may also select a program, e.g., from among a plurality of stored programs, as the present program (or one of a plurality of programs in a program group) to control delivery of stimulation by IMD 4.

IMD 4 and programmer 20 may communicate via wireless communication, as shown in FIG. 1. For example, clinician programmer and patient programmer may communicate with each other using any of a variety of local wireless communication techniques, such as RF communication according to the 802.11 or Bluetooth specification sets, infrared communication, e.g., according to the IrDA standard, or other standard or proprietary telemetry protocols. Programmer 20 may include a transceiver to facilitate bi-directional communication with IMD 4.

In some examples, as described in greater detail with respect to FIGS. 3 and 4 below, programmer 20 may be used to recharge a power source of IMD 4 using the techniques of this disclosure. That is, for example, programmer 20 may include one or more leads, inductive coils, or other components for recharging a power source of IMD 4, e.g., via transcutaneous inductive coupling or other electrical or electromagnetic coupling. Alternatively, a charging device (not shown) having more limited (or even no) programming capabilities may be used to recharge the power source of IMD 4. Programmer 20 may also receive a number of measurements from the IMD 4 that are used to control a charging session. According to the techniques of this disclosure, IMD 4 may be charged during a top-off period that is based on a capacity of the power source of IMD 4, as well as a state of charge of the power source. Additionally or alternatively, according to the techniques of this disclosure, IMD 4 may be charged during a top-off period that includes a charging termination parameter that is determined based on a duration of a previous charging session and/or an amount of charge that was administered to the power source during the previous charging session.

Figure 2:
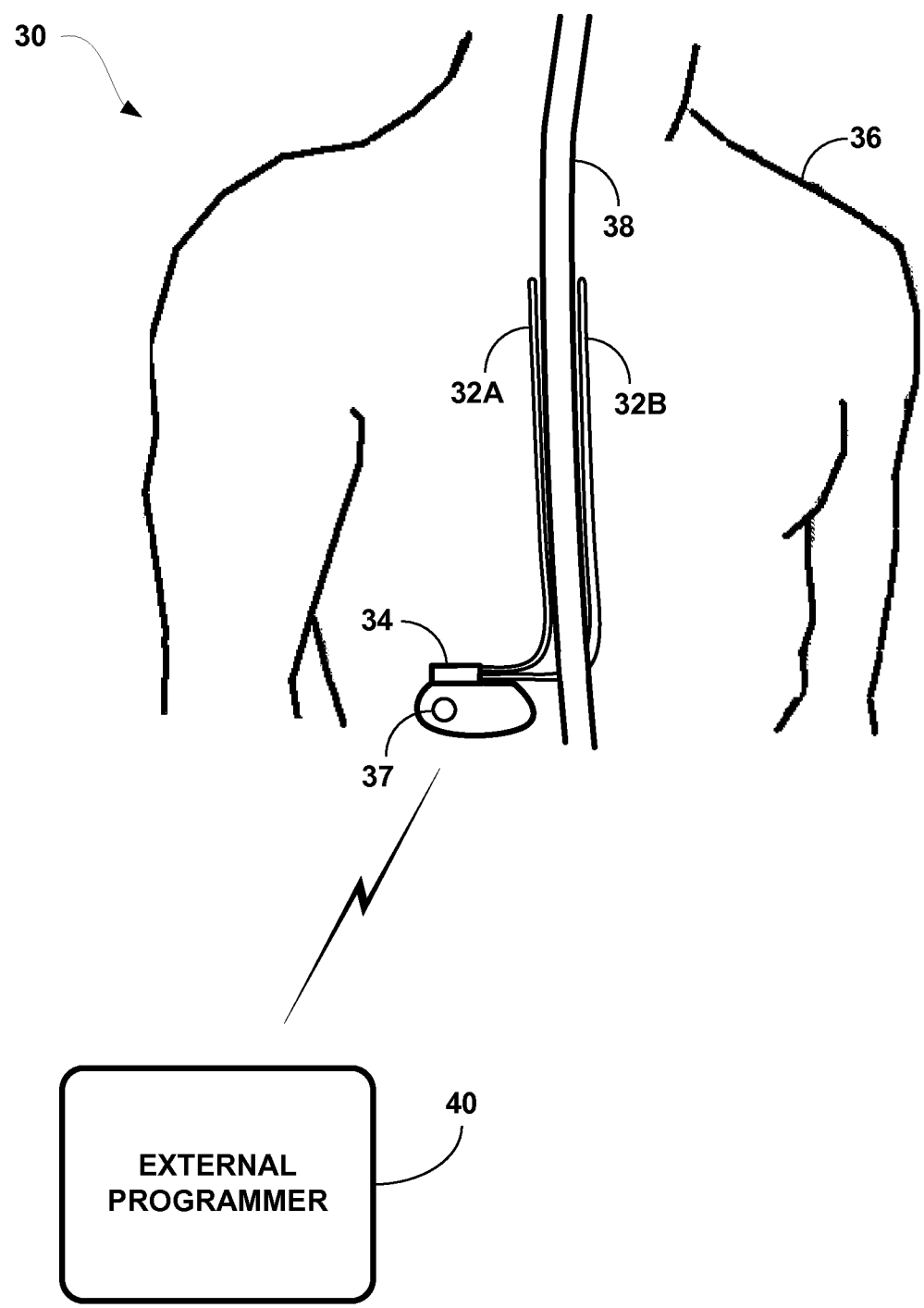
FIG. 2 is a conceptual diagram illustrating another example therapy system that includes an implantable stimulator coupled to a stimulation lead.

FIG. 2 is a conceptual diagram illustrating system 30 that delivers stimulation therapy to spinal cord 38 of patient 36 via implantable stimulator 34 (which may be referred to as IMD 34), with may implement the techniques of this disclosure. Other electrical stimulation systems may be configured to deliver electrical stimulation to gastrointestinal organs, pelvic nerves or muscle, peripheral nerves, or other stimulation sites. In the example of FIG. 2, system 30 delivers stimulation therapy from IMD 34 to spinal cord 38 via one or more electrodes (not shown) carried by, i.e., located on, implantable medical leads 32A and 32B (collectively "leads 32") as well as the housing of IMD 34, e.g., housing electrode 37.

System 30 and, more particularly, IMD 34 may operate in a manner similar to implantable stimulator 4 (FIG. 1). That is, in a current-based example, IMD 34 delivers controlled current stimulation pulses or waveforms to patient 36 via one or more regulated stimulation electrodes. Alternatively, IMD 34 may be configured to deliver constant voltage pulses. As mentioned above, in some examples, one of the electrodes may be unregulated.

In the example of FIG. 2, the distal ends of leads 32 carry electrodes that are placed adjacent to the target tissue of spinal cord 38. The proximal ends of leads 32 may be both electrically and mechanically coupled to IMD 34 either directly or indirectly via a lead extension and header. Alternatively, in some examples, leads 32 may be implanted and coupled to an external stimulator, e.g., through a percutaneous port. In additional example implementations, IMD 34 may be a leadless stimulator with one or more arrays of electrodes arranged on a housing of IMD 34 rather than leads that extend from the housing. Implantable leads 32 may have ring electrodes for purposes of illustration. However, other types of electrodes may be used.

IMD 34 may be implanted in patient 36 at a location minimally noticeable to the patient. For SCS, IMD 34 may be located in the lower abdomen, lower back, or other location to secure IMD 34. Leads 32 are tunneled from IMD 34 through tissue to reach the target tissue adjacent to spinal cord 38 for stimulation delivery. At the distal ends of leads 32 are one or more electrodes (not shown) that transfer the stimulation pulses from the lead to the tissue substantially simultaneously with stimulation pulses. Some of the electrodes may be electrode pads on a paddle lead, circular (i.e., ring), electrodes surrounding the body of leads 32, conformable electrodes, cuff electrodes, segmented electrodes, or any other type of electrodes capable of forming unipolar, bipolar or multi-polar electrode configurations. In an implantable stimulator, such as, for example, an implantable stimulator of FIG. 1 or FIG. 2, the stimulation pulses may be delivered using various electrode arrangements such as unipolar arrangements, bipolar arrangements or multipolar arrangements.

IMD 34 delivers stimulation to spinal cord 38 to reduce the amount of pain perceived by patient 36. As mentioned above, however, the stimulator may be used with a variety of different therapies, such as peripheral nerve stimulation (PNS), peripheral nerve field stimulation (PNFS), deep brain stimulation (DBS), cortical stimulation (CS), pelvic floor stimulation, peripheral nerve stimulation, gastric stimulation, and the like. The stimulation delivered by IMD 34 may take the form of stimulation pulses or continuous stimulation waveforms, and may be characterized by controlled current or voltage levels, as well as programmed pulse widths and pulse rates in the case of stimulation current pulses. Stimulation may be delivered via selected combinations of electrodes located on one or both of leads 32 and on the housing. Stimulation of spinal cord 38 may, for example, prevent pain signals from traveling through the spinal cord and to the brain of the patient. Patient 36 perceives the interruption of pain signals as a reduction in pain and, therefore, efficacious therapy.

With reference to FIG. 2, a user, such as a clinician or patient 36, may interact with a user interface of external programmer 40 to program IMD 34. Programming of IMD 34 may refer generally to the generation and transfer of commands, programs, or other information to control the operation of the stimulator. For example, programmer 40 may transmit programs, parameter adjustments, program selections, or other information to control the operation of IMD 34, e.g., by wireless telemetry.

As noted above, in some examples, programmer 40 may be used to recharge a power source of IMD 34 using the techniques of this disclosure. That is, for example, programmer 40 may include one or more leads, inductive coils, or other components for recharging a power source of IMD 34, e.g., via transcutaneous inductive coupling or other electrical or electromagnetic coupling. Alternatively, a charging device (not shown) having more limited (or even no) programming capabilities may be used to recharge the power source of IMD 34. Programmer 40 may also receive a number of measurements from the IMD 34 that are used to control a charging session. According to the techniques of this disclosure, IMD 34 may be charged during a top-off period that is based on a capacity of the power source of IMD 34, as well as a state of charge of the power source. Additionally or alternatively, according to the techniques of this disclosure, IMD 34 may be charged during a top-off period that includes a charging termination parameter that is determined based on a duration of a previous charging session and/or an amount of charge that was administered to the power source during the previous charging session.

Although the disclosure generally refers to implantable electrical stimulators for purposes of illustration, techniques described in this disclosure may be also used with other types of implantable medical devices, including implantable fluid delivery devices, such as insulin pumps, intra-thecal drug delivery pumps, or other devices that deliver medication or other fluids via one or more fluid delivery elements such as catheters. Such devices may provide fluid delivery therapy for chronic pain, diabetes, or any of a variety of other disorders. In each case, the device may include one or more therapy delivery elements such as one or more catheters implanted within a therapy region. In some cases, a pump may be fully implantable or may be an external device coupled to one or more percutaneously implanted catheters that extend into a therapy region. In some examples, the techniques of this disclosure may be also used with external neural stimulators, such as, for example, those used for "trialing" therapies and/or devices with a patient prior to implantation. Accordingly, description of implantable stimulators is provided for purposes of illustration and should not be considered limiting of the techniques as broadly described in this disclosure.

Figure 3:
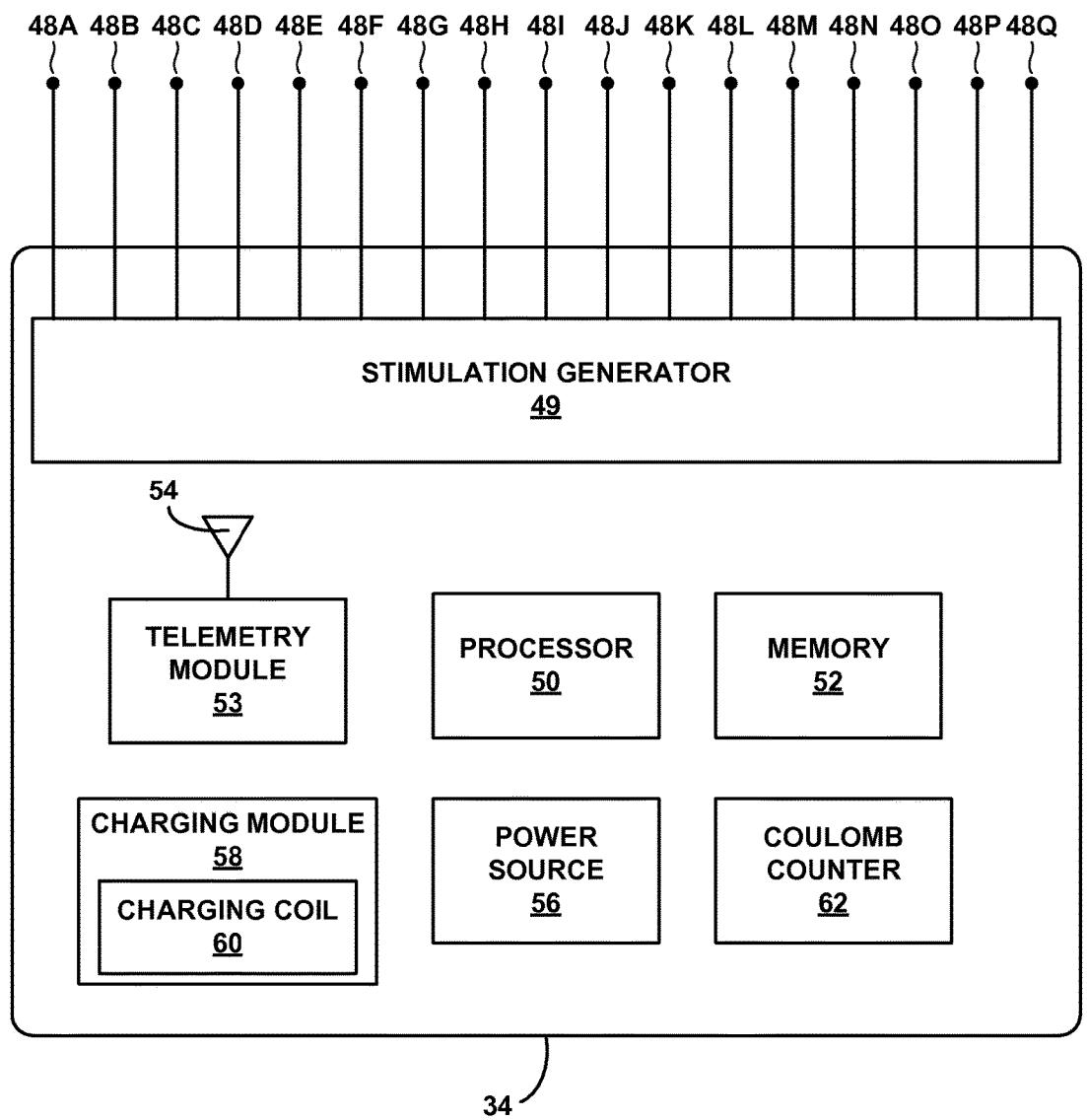
FIG. 3 is a block diagram illustrating various example components of an implantable electrical stimulator.

FIG. 3 is a block diagram illustrating various components of an example implantable stimulator, such as IMD 34 shown in FIG. 2, which may implement the techniques of this disclosure. Although the components shown in FIG. 3 are described in reference to IMD 34, such components may also be included within implantable stimulator 4 and used within system 2 (FIG. 1), or within another implantable stimulator. In the example of FIG. 3, IMD 34 includes electrodes 48A-48Q ("electrodes 48"), stimulation generator 49, processor 50, memory 52, telemetry module 53, antenna 54, power source 56, coulomb counter 62, charging module 58, and charging coil 60. It should be understood that, in other examples, IMD 34 may include more or fewer components than those shown in FIG. 3. For example, as described in greater detail below, power source 56 may be associated with one or more inductive coils not shown in FIG. 3 for purposes of clarity.

IMD 34 is also shown in FIG. 3 coupled to electrodes 48A-Q (collectively "electrodes 48"). Electrodes 48 may be implantable and may be deployed on one or more implantable leads. With respect to FIG. 1, lead segments 12A and 12B may carry electrodes 48A-H and electrodes 48I-P, respectively. In some cases, one or more additional electrodes may be located on or within the housing of IMD 34, e.g., to provide a common or ground electrode or a housing anode. With respect to FIG. 3, leads 32A and 32B may carry electrodes 48A-H and electrodes 48I-P, respectively. In the examples of FIGS. 1 and 2, a lead or lead segment carries eight electrodes to provide an 2×8 electrode configuration (two leads with 8 electrodes each), providing a total of sixteen different electrodes. The leads may be detachable from a housing associated with IMD 34, or be fixed to such a housing.

In other examples, different electrode configurations comprising a single lead, two leads, three leads, or more may be provided. In addition, electrode counts on leads may vary and may be the same or different from a lead to lead. Examples of other configurations include one lead with eight electrodes (1×8), one lead with 12 electrodes (1×12), one lead with 16 electrodes (1×16), two leads with four electrodes each (2×4), three leads with four electrodes each (3×4), three leads with eight electrodes each (3×8), three leads with four, eight, and four electrodes, respectively (4-8-4), two leads with 12 or 16 electrodes (2×12, 2×16), or other configurations. Different electrodes are selected to form electrode combinations. Polarities are assigned to the selected electrodes to form electrode configurations.

Electrode 48Q may represent one or more electrodes that may be carried on a housing, i.e., can, of IMD 34. Electrode 48Q may be configured as a regulated or unregulated electrode for use in an electrode configuration with selected regulated and/or unregulated electrodes among electrodes 48A-48P, which may be located on a lead body of one or more leads, as described above. Electrode 48Q may be formed together on a housing that carries the electrode and houses the components of IMD 34, such as stimulation generator 49, processor 50, memory 52, telemetry module 53, and power source 56.

In addition, electrode 48Q may be configured for use as an anode to source current substantially simultaneously with current sourced by one or more other electrodes 48A-48P to form a unipolar or omnipolar arrangement. By way of specific example, electrodes 48A, 48B, and electrode 48Q each could be configured for use as anodes. Electrodes 48A, 48B could deliver electrical stimulation current substantially simultaneously with the electrical stimulation current delivered via electrode 48Q. In this illustration, one or more cathodes could be formed with other electrodes (e.g., any of electrodes 48C-48P) on the leads to sink current sourced by anodes 48A, 48B and 48Q. Any of a variety of electrode arrangements such as unipolar, bipolar, multipolar, or omnipolar arrangements may be used to deliver stimulation. Accordingly, discussion of particular arrangements is provided for purposes of illustration which should not be considered limiting of the techniques broadly described in this disclosure.

Stimulation generator 49 is electrically coupled to electrodes 48A-P via conductors of the respective lead, such as lead 12 in FIG. 1 or leads 32 in FIG. 2, in implementations in which electrodes 48A-P are carried by, or located on, leads. Stimulation generator 49 may be electrically coupled to one or more housing ("can") electrodes 48Q via an electrical conductor disposed within the housing of IMD 34. Stimulation generator 49 may include stimulation generation circuitry to generate stimulation pulses or waveforms and circuitry for switching stimulation across different electrode combinations. For example, stimulation generator 49 may produce an electrical stimulation signal in accordance with a program based on control signals from a processor, such as processor 50.

Processor 50 may include one or more microprocessors, digital signal processors (DSPs), application-specific integrated circuits (ASICs), field-programmable gate arrays (FPGAs), or other digital logic circuitry. Processor 50 may control operation of IMD 34, e.g., controls stimulation generator 49 to deliver stimulation therapy according to a selected program or group of programs retrieved from a memory, such as memory 52 described below. For example, processor 50 may control stimulation generator 49 to deliver electrical signals, e.g., as stimulation pulses or continuous waveforms, with current amplitudes, pulse widths (if applicable), and rates specified by one or more stimulation programs. Processor 50 may control stimulation generator 49 based on parameters specified by programs downloaded from an external programmer such as, for example, programmer 20 (FIG. 1) or programmer 40 (FIG. 2). An external programmer, such as a clinician or patient programmer, may also specify that processor 50 should select one or more programs that have been downloaded to the implantable stimulator.

Upon selection of a particular program, processor 50 may control stimulation generator 49 to deliver stimulation according to the program. In some examples, multiple programs may be selected for separate program slots. Each program may specify a set of stimulation parameters, such as amplitude, pulse width and pulse rate, if applicable. For a continuous waveform, parameters may include amplitude and frequency. In addition, each program may specify a particular electrode combination for delivery of stimulation, and an electrode configuration in terms of the polarities and regulated/unregulated status of the electrodes. The electrode combination may specify particular electrodes in a single array or multiple arrays, and on a single lead or among multiple leads. According to aspects of this disclosure, processor 50 may also control charging of power source 56. For example, processor 50 may control charging module 58 when charging power source 56.

Memory 52 may store instructions for execution by processor 50, stimulation therapy data, sensor data, and/or other information regarding therapy for patient 6. Memory 52 may comprise one or more computer-readable storage media. Examples of memory 52 include, but are not limited to, a random access memory (RAM), a read only memory (ROM), an electrically erasable programmable read-only memory (EEPROM), a magnetic storage device, flash memory, or any other medium that can be used to store desired program code in the form of instructions or data structures and that can be accessed by a computer or a processor. Memory 52 may, in some examples, be considered as a non-transitory storage medium. In certain examples, a non-transitory storage medium may store data that can, over time, change (e.g., in RAM).

As noted above, in some examples, memory 52 may store program instructions that, when executed by processor 50, cause the processor to perform various functions ascribed to processor 50 and IMD 34 in this disclosure. Memory 52 may also store a patient profile and information regarding therapy that the patient 6 had previously received. Storing such information may be useful for subsequent treatments such that, for example, a clinician may retrieve the stored information to determine the therapy applied to the patient during his/her last visit. The information may be modified and updated by a user of a programmer.

Telemetry module 53 may include a radio frequency (RF) transceiver to facilitate bi-directional communication between IMD 34 and a programmer, such as programmer 40 (FIG. 2). Telemetry module 53 may include an antenna 54 that may take on a variety of forms. For example, antenna 54 may be formed by a conductive coil or wire embedded in a housing associated with IMD 34. Alternatively, antenna 54 may be mounted on a circuit board carrying other components of IMD 34 or take the form of a circuit trace on the circuit board. In this way, telemetry module 53 may facilitate communication with programmer 40 to receive, for example, new programs or adjustments to programs.

Power source 56 may be any unit that provides power to the components of IMD 34 by discharging charge that is stored within power source 56. In some examples, power source 56 may be a rechargeable battery and may be coupled to power circuitry. That is, power source 56 may be one or more rechargeable batteries that are tied together in parallel or in series to form a single power source. In another example, power source 56 may comprise one or more single use batteries (e.g., non-rechargeable), one or more capacitors, and/or supercapacitors. In addition, while shown in FIG. 3 as a single power source 56, IMD 34 may include multiple different power sources 56. Accordingly, in examples in which IMD 34 includes multiple different power sources, aspects of this disclosure may be extendable to each power source.

As noted above, power source 56 may include one or more a rechargeable batteries or a non-rechargeable battery or batteries, e.g., one or more primary cell batteries. Examples of power source 56 include, but are not limited to, lead acid batteries, nickel cadmium (NiCad) batteries, nickel metal hydride (NiMH) batteries, lithium ion (Li-ion) batteries, and lithium ion polymer (Li-ion polymer) batteries.

Power source 56 may provide power to one, some, or all of the various components of IMD 34. Accordingly, power source 56 may be discharged due to the power consumed by the various components of IMD 34 (e.g., such as stimulation generator 49, processor 50, telemetry module 53, or any other component of IMD 34). Due to the discharging, power source 56 may need to be recharged or replaced periodically to ensure that power source 56 does not fully drain. As described in greater detail below, aspects of this disclosure relate to recharging power source 56. More specifically, certain aspects of this disclosure may relate to recharging power source 56 during a top-off period, typically toward the end of a charging session.

Charging module 58 may facilitate charging of power source 56. For example, power source 56 may be rechargeable via electrical or electromagnetic coupling, such as inductive coupling, or ultrasonic energy transmission, and may include an appropriate circuit for recovering transcutaneously received energy. In the example shown in FIG. 3, charging module 58 includes charging coil 60 for inductive energy transfer. In some examples, charging module 58 may also include a rectifier circuit, as well as a rechargeable circuit and a power generation circuit to produce the operating power. Recharging may be accomplished through proximal inductive interaction between an external charger (e.g., included in programmer 40 or a charging device) and charging coil 60. In some examples, power requirements may be small enough to allow IMD 34 to utilize patient motion at least in part and implement a kinetic energy-scavenging device to trickle charge power source 56.

In general, coulomb counter 62 may monitor the charge delivered by power source 56 and/or the charge received by power source 56 (e.g., upon recharging). For example, coulomb counter 62 may be initialized to zero. In some examples, for every unit of charge that is received by power source 56, coulomb counter 62 may increment a counter by one. For example, during charging of power source 56, coulomb counter 62 may count each unit of charge (e.g., in coulombs) delivered to power source 56. Alternatively, for every unit of charge delivered by power source 56, coulomb counter 62 may decrement a counter by one. That is, for example, when providing a therapy via stimulation generator 49, coulomb counter may count each unit of charge (e.g., in coulombs) delivered by power source 56. In some examples, to count the amount of charge delivered and/or received by power source 56, coulomb counter 62 may integrate the amount of current delivered by power source 56 over time.

Accordingly, in some examples, coulomb counter 62 may be positioned at the output of power source 56 to accurately reflect the amount of current or charge being delivered to stimulation generator 49 during therapy and/or may be positioned at the input of power source to reflect the amount of current or charge being received by/administered to power source 56 during a charging session. In some examples, coulomb counter 62 may comprise two coulomb counters, with one determining the amount of current or charge delivered by power source 56 and the other determining the amount of current or charge delivered to power source 56 so that the overall charge stored by power source may be determined. If coulomb counter 62 is configured to measure coulombs, the actual amount of charge transferred to the electrodes may be determined. If current is measured, the integral of current over the time that stimulation is delivered will yield the number of milliamp-hours. In either event, using the relationship that one coulomb equals approximately 0.00027778 amp-hours, the charge delivered and/or received by power source 56 may be determined.

According to the techniques of this disclosure, IMD 34 may be charged during a top-off period that is based on a capacity of power source 56, as well as a state of charge of power source 56. Additionally or alternatively, according to the techniques of this disclosure, IMD 34 may be charged during a top-off period that includes a charging termination parameter that is determined based on a duration of a previous charging session and/or an amount of charge that was administered to power source 56 during the previous charging session.

For example, a charging top-off period typically occurs during the end of a charging session (e.g., as power source 56 approaches full charge). The top-off period may help to charge power source 56 to full capacity, while also reducing the risk of raising the voltage of power source 56 beyond a desirable level. That is, during charging, an impedance of power source 56 may increase as power source 56 reaches full charge. To avoid a corresponding rise in voltage, which may cause power source 56 to swell and/or become unstable, a charging current may be reduced during a top-off period. In this way, power source 56 may be fully charged without increasing the voltage of power source 56 in a potentially undesirable way.

According to aspects of this disclosure, IMD 34 may estimate the capacity of power source 56 based on an amount of charge applied to power source 56 during a previous charging session. For example, coulomb counter 62 may track an amount of charge that is expended by IMD 34, as well as an amount of charge that is stored by power source 56 during a charging session, assuming power source 56 is fully charged during each charging session. Accordingly, IMD 34 may estimate a new capacity for power source after each charging session, based on the amount of charge that was expended versus the amount of charge that was administered during the charging session. In this way, IMD 34 may adjust the capacity of power source 56 as power source 56 degrades and is able to store relatively less charge.

IMD 34 may determine the state of charge of power source 56 relative to the capacity of power source 56. In some examples, IMD 34 may use coulomb counter 62 to determine the state of charge. That is, IMD 34 may determine the number of coulombs (or current) being received by power source 56 from charging module 58 relative to the capacity of power source 56. According to aspects of this disclosure, IMD 34 may reduce the charging current that is applied to power source 56 from charging module 58 in response to the state of charge of power source 56 approaching the capacity of power source 56.

As noted above, according to the techniques of this disclosure, IMD 34 may additionally or alternatively be charged during a top-off period that includes a charging termination parameter that is determined based on a duration of a previous charging session and/or an amount of charge that was administered to power source 56 during the previous charging session. Examples of charging termination parameters may include a minimum charging current cut off, a power level cut off, or other parameters that indicate when power source 56 has reached full charge (e.g., impedance of power source 56, and the like).

A minimum charging current cut off may be associated with the smallest current at which IMD 34 is allowed to charge power source 56. That is, for example, it may not be beneficial to charge power source 56 using a charging current that is lower than the minimum charging current, as power source 56 may not be effectively charged, the charging session may be longer in duration than desired, and the like. A power level cut off may be associated with a minimum power with which power source 56 may be charged, which may occur when power source 56 has been fully recharged or nearly fully recharged. For example, as described below, as power source 56 approaches full charge, the power used to charge the power source 56 may be reduced (e.g., during a top-off period). The power cut off value may be a minimum power level that is used for charging power source 56. The power cut off value may be set such that the power level cut off occurs as power source 56 reaches full charge. In some instances, the power level cut off value may be measured by programmer 40 or anther charging device responsible for applying a charge to power source 56. That is, the power level cut off value may be a minimum output power of the charging device.

According to aspects of this disclosure, IMD 34 may initially determine a duration of a previous charging session, as well as, in some examples, an amount of charge that was administered to power source 56 by charging module 58 during the previous charging session. The duration may be measured by timing the previous charging session. The amount of charge administered to power source 56 by charging module 58 may be determined, for example, using coulomb counter 62.

IMD 34 may then determine a new minimum charging current cut off (e.g., for the next charging session) based on the duration of the previous charging session and/or the amount of charge administered during the previous charging session. For example, according to aspects of this disclosure, if the amount of charge delivered during the previous charging session does not charge power source 56 to full or nearly full capacity, IMD 34 may adjust a charging termination parameter, such as lower the minimum charging current cut off. Lowering the minimum charging current cut off may increase the duration of the top-off period and allow more charge to be administered to power source 56, i.e., by permitting the current to be delivered for a longer period of time.

Additionally or alternatively, according to aspects of this disclosure, IMD 34 may compare the duration of the previous charging session to a predefined target duration. If the duration of the previous charging session was shorter than the target duration (e.g., power source 56 completed charging in less time than the target duration), IMD 34 may adjust the charging termination parameter allow power source 56 to be charged for a longer duration (e.g., charged using a lower minimum charging current cut off). Alternatively, if the duration of the previous charging session was longer than the target duration, IMD 34 may adjust the charging termination parameter to shorten the charging duration.

While IMD 34 shown in FIG. 3 is described as carrying out certain techniques of this disclosure, e.g., charging IMD 34 during a top-off period, it should be understood that the techniques of this disclosure may be performed by a single device or by multiple devices. That is, in some examples as described above, IMD 34 may be responsible for controlling charging parameters (e.g., charging based on a state of charge and a capacity of power source 56, altering a minimum charging current cut off, and the like). In other examples, IMD 34 may provide certain data (e.g., charging current, state of charge, voltage, and the like) to programmer 40 (or another charging device), thereby allowing programmer 40 to control charging parameters. In still other examples, IMD 34 and programmer 40 may each be responsible for controlling charging functions.

Figure 4:
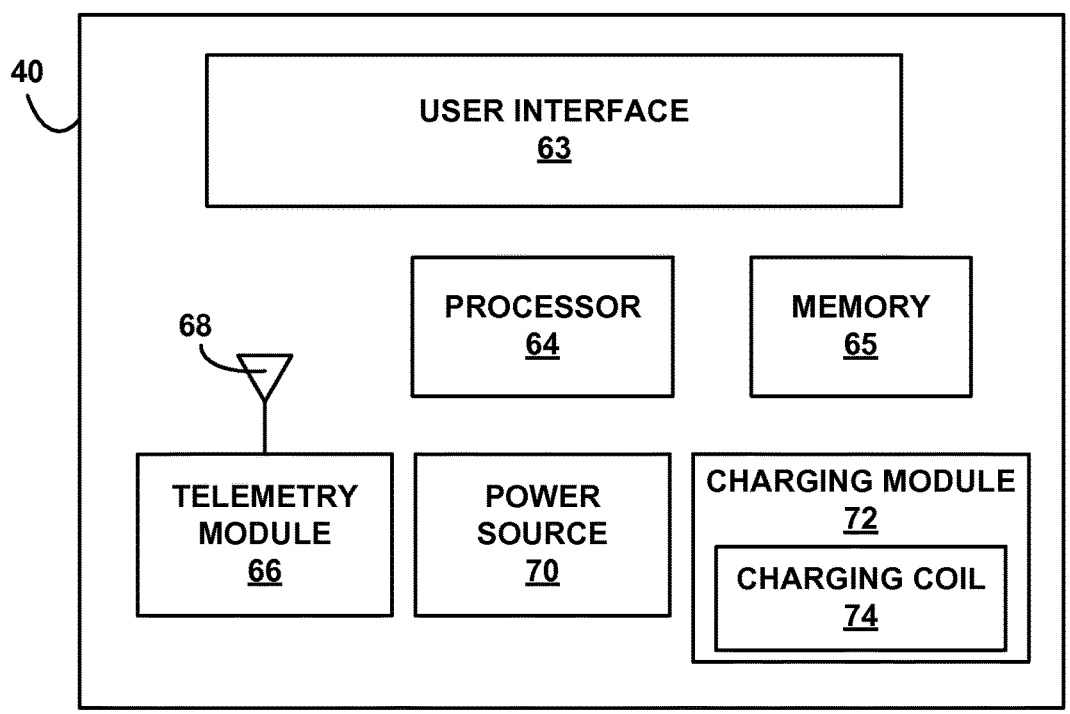
FIG. 4 is a block diagram illustrating various example components of an external programmer for an implantable electrical stimulator.

FIG. 4 is a functional block diagram illustrating various components of an external programmer for an implantable stimulator, such as IMD 4 (FIG. 1) and/or IMD 34 (FIG. 2). Although the components shown in FIG. 4 are described in reference to external programmer 40 shown in FIG. 2, it should be understood that the components may also be included within a programmer 20 (FIG. 1), or another clinician programmer and/or patient programmer.

As shown in FIG. 4, external programmer 40 includes user interface 63, processor 64, memory 65, telemetry module 66, antenna 68, power source 70, and charging module 72 having charging coil 74. The components shown in FIG. 4 are provided for purposes of example only, and other external programmers may include more or fewer components than those shown in FIG. 4.

A clinician or patient 6 interacts with user interface 63 in order to, for example, manually select, change or modify programs, e.g., by adjusting voltage or current amplitude, adjusting pulse rate, adjusting pulse width, or selecting different electrode combinations, polarities, or configurations, and may provide efficacy feedback or view stimulation data. User interface 63 may include a screen and one or more input hard and/or soft key buttons that allow external programmer 20 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

The user interface 63 may also display information associated with a charging session, in examples in which programmer 20 is used to charge a rechargeable power source of an implantable stimulator, such as power source 56. For example, user interface 63 may display information indicating a total remaining charge of power source 56. User interface 63 may also display a timer that tracks how long a particular charging session has lasted. In some examples, user interface 63 may indicate a charging current used to charge power source 56 (e.g., in milliamps (mA)). User interface 63 may also indicate a state of charge (e.g., in milliamp-hours (mAh) or as a percentage of total charge), as well as when the power source 56 has been fully charged.

In general, processor 64 controls user interface 63, stores and retrieves data to and from a memory (e.g., such as memory 65 described below), and controls an exchange of data with IMD 34 via telemetry module 66 and antenna 68. Processor 64 may take the form of one or more microprocessors, controllers, DSPs, ASICS, FPGAs, or equivalent discrete or integrated logic circuitry. The functions attributed to processor 64 herein may be embodied as software, firmware, hardware or any combination thereof.

Memory 65 may store instructions that cause processor 64 to provide various aspects of the functionality ascribed to external programmer 20 herein. Memory 65 may include any fixed or removable magnetic, optical, or electrical media, such as RAM, ROM, CD-ROM, magnetic disks, EEPROM, or the like. Memory 65 may also include a removable memory portion that may be used to provide memory updates or increases in memory capacities. A removable memory may also allow patient data to be easily transferred to another computing device, or to be removed before programmer 20 is used to program therapy for another patient. Memory 65 may also store information that controls operation of IMD 34, such as therapy delivery values and/or charging parameters.

Telemetry module 66 allows the transfer of data to and from IMD 34. Telemetry module 66 may communicate automatically with IMD 34 at a scheduled time or when the telemetry module 66 detects the proximity of the stimulator. Alternatively, telemetry module 66 may communicate with IMD 34 when signaled by a user through user interface 63. To support RF communication, telemetry module 66 may include appropriate electronic components, such as amplifiers, filters, mixers, encoders, decoders, and the like. As described with respect to FIG. 3 above, telemetry module 66 may include an antenna 68 that may take on a variety of forms. For example, antenna 68 may be formed by a conductive coil or wire embedded in a housing associated with programmer 20. Alternatively, antenna 68 may be mounted on a circuit board carrying other components of programmer 20 or take the form of a circuit trace on the circuit board. In accordance with this disclosure, programmer 40 may communicate with IMD 34, via telemetry module 66 to retrieve information during a charging session.

Power source 70 delivers operating power to the components of programmer 40. Power source 70 may be a rechargeable battery, such as a lithium ion or nickel metal hydride battery. Other rechargeable or conventional batteries may also be used. In some cases, external programmer 20 may be used when coupled to an alternating current (AC) outlet, i.e., AC line power, either directly or via an AC/DC adapter. Power source 70 may include circuitry to monitor energy remaining within a battery in the programmer 40. In this manner, user interface 63 may provide a current battery level indicator or low battery level indicator when the battery of programmer 40 needs to be replaced or recharged. In some cases, power source 70 may be capable of estimating the remaining time of operation using the current battery.

Charging module 72 may be used to recharge a rechargeable battery of an implantable stimulator, such as IMD 34. Charging module 72 may receive charge from one or more power sources, such as a wired power connection or one or more batteries (e.g., rechargeable or non-rechargeable). In the example shown in FIG. 4, charging module 72 includes charging coil 74 for inductive energy transfer. In some examples, charging coil 74 may be an external coil that may be placed on the surface of the skin of patient 36 in proximity to a coil of an implanted device, such as IMD 34, to perform inductive energy transfer. Thus, in some examples, charging module 72 may be configured to transcutaneously charge a power source of an implantable stimulator, such as power source 56, e.g., without a direct physical connection via leads or other wires. In some examples, charging module 72 may be integrated with telemetry module 66, but is shown separately in FIG. 4 for purposes explanation.

In some examples, as described above with respect to FIG. 3, IMD 34 may be responsible for controlling charging. In other examples, however, programmer 40 or some other charging device may be responsible for carrying out charging. For example, processor 64 may be responsible for monitoring charging parameters and controlling charging module 72. That is, programmer 40 may receive certain data from IMD 34 and may control a charging session based on the received data. In an example, IMD 34 may send data such as charging current, state of charge, voltage, capacity, and the like to programmer 40. Upon receiving the feedback data, programmer 40 may adjust output power at charging module 72 and charging coil 74.

Additionally or alternatively, in some examples, IMD 34 and programmer 40 may collaboratively control a charging session. For example, IMD 34 may monitor a voltage of power source 56 during charging, and shunt excess current (e.g., divert to a resistive load) if the voltage increases beyond a predetermined limit. In this example, IMD 34 may report the voltage limit condition to programmer 40, which may use the received data to alter the charging parameters (e.g., reduce output power at charging module 72 and charging coil 74). After adjusting the charging parameters such that IMD 34 is no longer shunting charging current, programmer 40 may determine whether to continue charging.

Accordingly, in some examples, programmer 40 may implement the techniques of this disclosure. For example, programmer 40 may implement a top-off period that is based on a capacity of a power source and a state of charge of the power source of an implantable stimulator, such as IMD 34. Additionally or alternatively, programmer 40 may implement a top-off period that includes a charging termination parameter that is determined based on a duration of a previous charging session and/or an amount of charge that was administered to the power source during the previous charging session.

Figure 5:
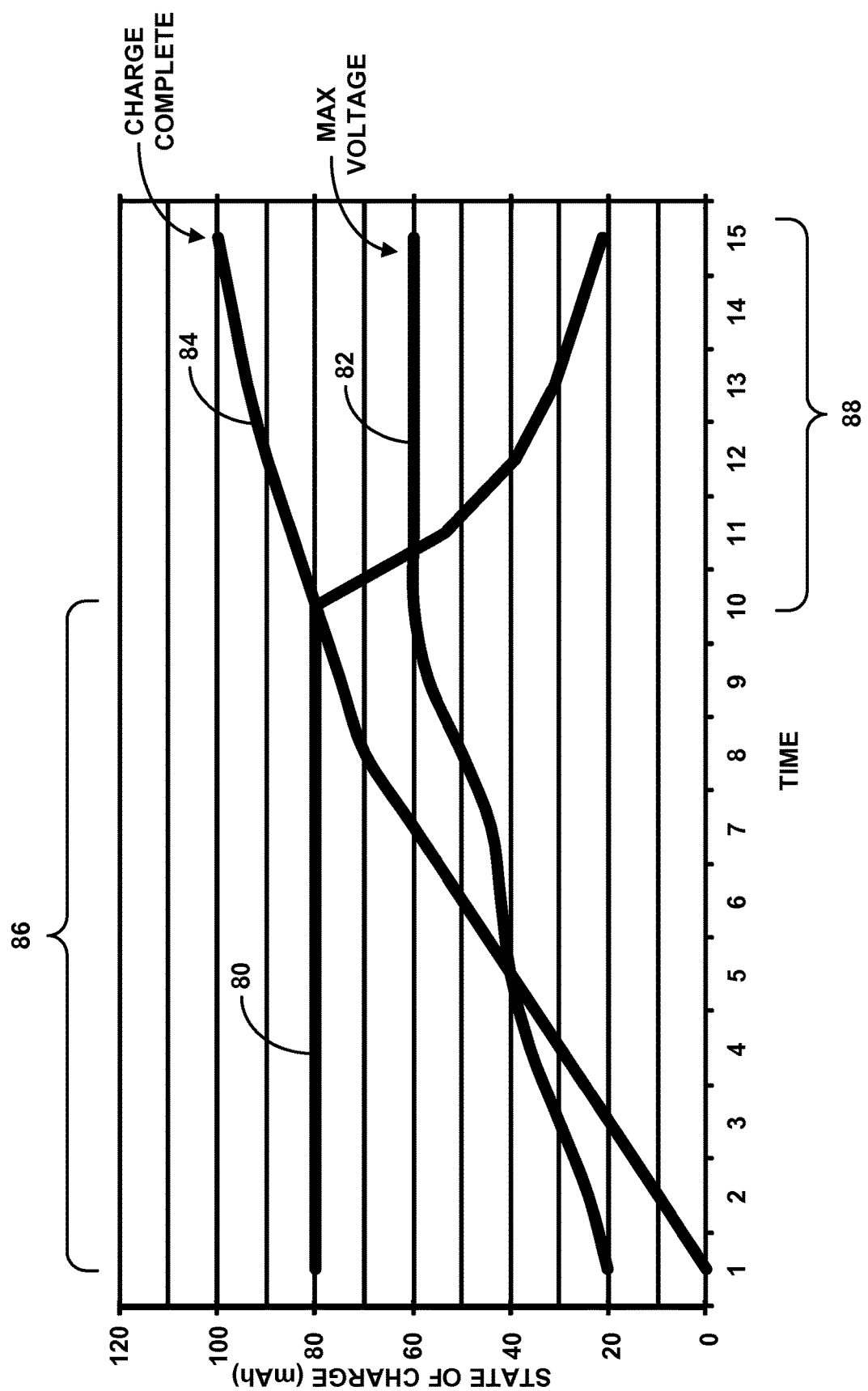
FIG. 5 is a graph illustrating an example charging session having a top-off period.

FIG. 5 is a graph illustrating an example charging session having a top-off period. For example, FIG. 5 generally illustrates an example charging session in which a voltage limit is used during a top-off period to control a charging current applied to a power source (e.g., a battery). For example, as noted above, a charging top-off period typically occurs during the end of a charging session, and may help to charge the power source to full capacity without increasing the voltage of the power source beyond a desirable level. That is, during charging, an impedance of the power source may increase as the power source reaches full charge. To avoid a corresponding rise in voltage, a charging current may be reduced during a top-off period. In the example shown in FIG. 5, the top-off may be triggered by the voltage reaching the voltage limit. The top-off period then continues until the power source has reached full charge.

Although generally described as being performed by components of IMD 34 (FIGS. 2, 3) and programmer 40 (FIGS. 2, 4) for purposes of explanation, it should be understood that other implantable stimulators and programmers, such as implantable stimulator 4 and programmer 20 (FIG. 12), or a variety of other devices may also be configured to perform the charging session shown in FIG. 5. Moreover, in other examples, IMD 34 and/or programmer 40 may perform different functions than those described with respect to FIG. 5 (e.g., IMD 34 may perform functions attributed to programmer 40, and vice versa).

The example graph shown in FIG. 5 tracks a charging current 80, a voltage 82, and a state of charge 84 throughout a charging session of power source 56. That is, for example, charging current 80 corresponds to a current induced in charging coil 60 of charging module 58 and applied to power source 56. In the example shown in FIG. 5, IMD 34 measures charging current 80, which is represented in milliamps (mA). Voltage 82 corresponds to a voltage measured at power source 56, which may be measured in volts (V). In addition, state of charge 84 corresponds to a state of charge of power source 56, which may be measured in milliamp-hours (mAh). In other examples, state of charge 84 may also be represented as a percentage of the capacity of power source 56 (e.g., 50% of full charge). In some examples, IMD 34 may relay this data to programmer 40 (or another charging device) during a charging session.

As shown in FIG. 5, programmer 40 applies a charging current 80 to power source 56 during an initial charging period 86, e.g., via inductive coils and suitable charging circuitry within programmer 40 and within IMD 34. During the initial charging period 86, programmer 40 may apply a maximum charging current (e.g., as measured at power source 56) to power source 56 in order to charge power source 56 as quickly as possible without damaging power source 56. In the example shown in FIG. 5, programmer 40 applies a current that, upon inductive transfer, induces a maximum charging current of approximately 80 milliamps (mA), as applied to power source 56, during the initial charging period 86. In other examples, the maximum charging current may vary depending on, for example, the capabilities of power source 56, the capabilities of programmer 40, or other factors.

In the example shown in FIG. 5, IMD 34 initiates a top-off period 88 upon the voltage 82 of power source 56 reaching a voltage limit ("max voltage"). For example, IMD 34 may indicate to programmer 40 that IMD 34 has reached the voltage limit. The voltage limit may be reached, for example, due to rising impedance in power source 56 as power source 56 is charged. That is, if a constant maximum charging current is applied to power source 56, as impedance in power source 56 increases voltage also increases.

When the voltage limit is reached, programmer 40 may begin to top-off power source 56 of IMD 40 using a lower charging current (e.g., via charging module 72 and charging coil 74) in an attempt to maximize the charge delivered to power source 56. The voltage limit that triggers top-off may be a predefined voltage level that is intended to protect power source 56 from swelling or otherwise becoming unstable during charging. In the example shown in FIG. 5, the voltage 82 reaches the voltage limit at a state of charge 84 of approximately 80 mAh.

During the top-off period 88, IMD 34 shunts the charging current 80 such that less than the maximum charging current is used to charge power source 56. That is, power source 56 shunts the charging current 80 (e.g., prevents charging current from increasing) as power source 56 reaches full charge in order to maintain the voltage 82 of power source 56 at the voltage limit. In some examples, IMD 34 may shunt the charging current, for example, by diverting the charging current to a resistive load. In other examples, IMD 34 may increase the resistive path between power source 56 and charging coil 60 in an effort to divide the voltage between internal impedance of power source 56 and the charging circuitry of IMD 34. In other examples, IMD 34 may communicate with programmer 40 to lower the charging current that is applied by charging coil 74 of charging module 72 to charging coil 60 of charging module 58.

Programmer 40 may stop charging power source 56 upon determining that power source 56 has reached full charge. That is, IMD 34 may relay to programmer 40 that power source 56 has reached full charge, and programmer 40 may end the charging session. In some examples, as described in greater detail below, programmer 40 may determine that power source 56 has reached full charge upon reducing the charging current to a minimum allowed charging current. That is, programmer may stop charging power source 56 when the charging current declines (during top-off) to a minimum charging current. In other examples, programmer 40 may determine that power source 56 has reached full charge differently (e.g., using coulomb counter 62).

IMD 34 may initiate top-off period 88 and reduce charging current 80 based on reaching the voltage limit alone. However, this may not account for variation and/or changing characteristics of power source 56 (e.g., such as impedance). That is, for example, due to differing impedance profiles of power sources, a first power source 56 having a relatively higher impedance than a second power source 56 may begin top-off period 88 relatively earlier in the charging session than the second power source 56, regardless of the state of charge of the power source 56.

Figure 6:
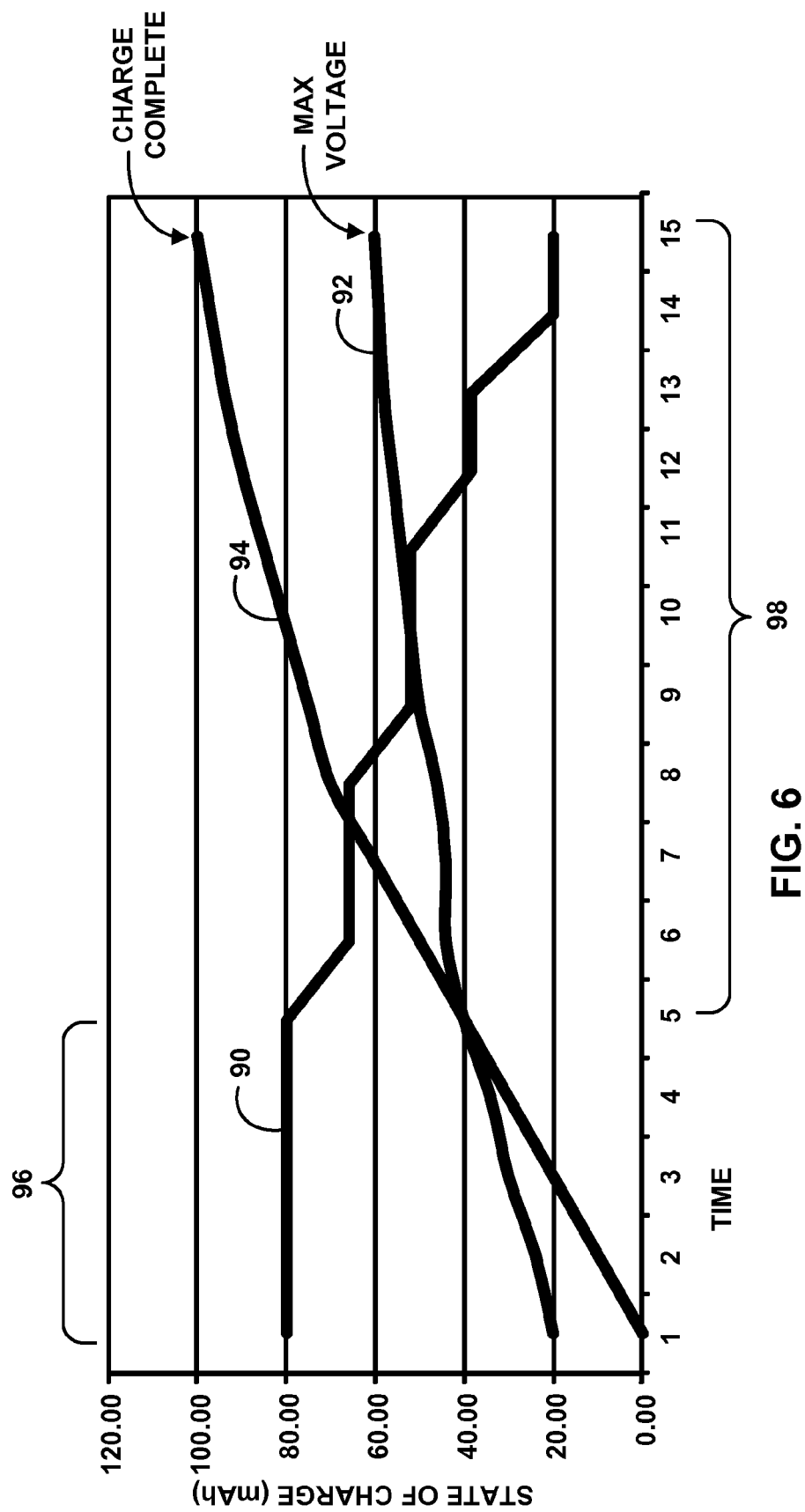
FIG. 6 is a graph illustrating another example charging session having another top-off period.

FIG. 6 is a graph illustrating another example charging session having another top-off period, which may be performed according to aspects of this disclosure. For example, FIG. 6 generally illustrates an example charging session in which charging during a top-off period may be based on battery capacity and battery state of charge, according to aspects of this disclosure. Although generally described as being performed by components of IMD 34 (FIGS. 2, 3) and programmer 40 (FIGS. 2, 4) for purposes of explanation, it should be understood that other implantable stimulators and programmers, such as implantable stimulator 4 and programmer 20 (FIG. 1), or a variety of other devices may also be configured to perform the charging session shown in FIG.

6. Moreover, in other examples, IMD 34 and/or programmer 40 may perform different functions than those described with respect to FIG. 5 (e.g., IMD 34 may perform functions attributed to programmer 40, and vice versa).

As with the example shown in FIG. 5, the example graph shown in FIG. 6 tracks a charging current 90, a voltage 92, and a state of charge 94 throughout a charging session of power source 56. As shown in FIG. 6, programmer 40 applies a charging current 90 to power source 56 during an initial charging period 96, e.g., via inductive coils and suitable charging circuitry within programmer 40 and within IMD 34. In the example shown in FIG. 6, programmer 40 applies a current that, upon inductive transfer, induces a maximum charging current of approximately 80 milliamps (mA) during the initial charging period 96. In other examples, the maximum charging current may vary depending on, for example, the capabilities of power source 56, the capabilities of programmer 40, or other factors.

The example shown in FIG. 6 includes a top-off period 98 based on a capacity of power source 56 and the state of charge 94 of the power source. Top-off period 98 may be initiated by IMD 34 or programmer 40.

In some examples, IMD 34 may measure state of charge 94 using coulomb counter 62. For example, as noted above with respect to FIG. 3, coulomb counter 62 may be positioned at the output of power source 56 for measuring the amount of charge, coulombs, or current being delivered to stimulation generator 49 during therapy and/or the amount of charge, coulombs, or current being received by power source 56 during a charging session. For example, coulomb counter 62 may count each unit of charge that is discharged by power source 56, while also counting each unit of charge that is received by power source 56 during charging.

Accordingly, according to aspects of this disclosure, IMD 34 may track the state of charge 94 of power source 56 relative to the capacity of power source 56. Thus, IMD 34 may estimate or otherwise recalibrate the capacity of power source 56 after each charging session. For example, IMD 34 may estimate the capacity of power source 56 for a current charging session based on an amount of charge applied to power source 56 during a previous charging session.

In some examples, coulomb counter 62 of IMD 34 may track an amount of charge that is expended by power source 56, as well as an amount of charge that is stored by power source 56 during a charging session, assuming power source 56 is fully charged during each charging session. Accordingly, IMD 34 may estimate a new battery capacity after each charging session, based on the amount of charge that was expended during therapy versus the amount of charge that was applied during the charging session. In this way, IMD 34 may adjust the capacity of power source 56 as power source 56 degrades over time and is able to store relatively less charge. Other methods may also be used to determine the capacity of power source 56.

In the example shown in FIG. 6, IMD 34 begins top-off period 98 upon state of charge 94 reaching approximately 40 mAh, or approximately 40% of charge for a power source 56 having a capacity of 100 mAh. For example, as noted above, a charging top-off period typically occurs during the end of a charging session, and may help to charge power source 56 to full capacity without increasing the voltage of power source 56 beyond a desirable level. In the example shown in FIG. 6, the top-off may be triggered based on the state of charge of power source 56.

While FIG. 6 illustrates IMD 34 beginning top-off period 98 at approximately 40% state of charge 94, in other examples, IMD 34 may begin top-off period 98 earlier (e.g., 35% of capacity, 30% of capacity, 25% of capacity, and the like) or later (e.g., 50%, 60%, 80%, and the like) during the charging session. The point at which IMD 34 begins top-off period 98 may vary based on, for example, the configuration/capability of power source 56, the age of power source 56, the capability of programmer 40, or other factors. For example, as the age of power source 56 increases, the impedance of power source 56 may also increase (e.g., a battery's impedance may rise over time). Accordingly, IMD 34 may begin top-off period 98 earlier (e.g., at a lower state of charge 94) for an older power source 56 than for a newer power source 56 in order to maintain voltage 92 at or below a voltage limit ("max voltage").

During top-off period 98, IMD 34 may reduce charging current 90 used to charge power source 56 as state of charge 94 approaches full capacity ("charge complete"). In some examples, IMD 34 may incrementally reduce charging current 90 during top-off period 98 as state of charge 94 approaches full capacity. That is, in the example shown in FIG. 6, IMD 34 incrementally reduces ("steps down") charging current 90 four times, with a period of constant charging current 90 between each step during top-off period 98. In some examples, the step sizes may be preprogrammed in IMD 34. In other examples, IMD 34 may adapt the step sized based on a rate at which voltage 92 of power source 56 is rising, a rate at which state of charge 94 is rising, or other factors. For example, if voltage 92 of power source 56 is rising relatively rapidly, IMD 34 may increase the step size in an effort to slow the rise in voltage.

In other examples, IMD 34 may step down charging current more or less frequently than that shown in FIG. 6 (e.g., two steps, three steps, six steps, and the like). Additionally or alternatively, IMD 34 may step down charging current 90 more or less quickly than that shown in FIG. 6. That is, in another example, IMD 34 may transition between a higher charging current 90 and a lower charging current 90 immediately (e.g., characterized by a vertical decline between steps) during top-off period 98. In yet another example, IMD 34 may transition between a higher charging current 90 and a lower charging current 90 more slowly than that shown in FIG. 6 (e.g., characterized by a more gradual decline between steps) during top-off period 98. In still other examples, IMD 34 may continually and gradually lower charging current 90 during top-off period 96 (e.g., without "steps").

According to the techniques of this disclosure, IMD 34 may continue charging power source 56 until a minimum charging current 90 is reached. The minimum charging current 90 may be the smallest current at which IMD 34 is allowed to charge power source 56. Minimum charging current 90 may be reached due to IMD 34 reducing charging current 90 as power source 56 reaches a full charge (e.g., according to state of charge 94). As noted above, reducing charging current 90 may help to maintain voltage 92 at or below a voltage limit. In other examples, another charging termination parameter may be used to indicate when charging is complete.

The minimum charging current may be predefined, or may be adapted based on power source 56 (e.g., as described below with respect to FIGS. 10-11). As shown in the example of FIG. 6, by reducing the charging current 90 based on state of charge 94 and the capacity of power source 56, current shunting (e.g., an internal diversion of charging current to a resistive load) can be avoided. That is, for example, IMD 34 may lower charging current 90 based on state of charge 94 and the capacity of power source 56 while maintaining voltage 92 equal to or lower than a voltage limit (e.g., "max voltage"). In the example shown in FIG. 6, the max voltage is not reached until power source 56 has completed charging (e.g., state of charge 94 reaches "charge complete"). Thus, according to the techniques of this disclosure, IMD 34 may charge power source 56 using the largest charging current possible while also avoiding current shunting.

Figure 7:
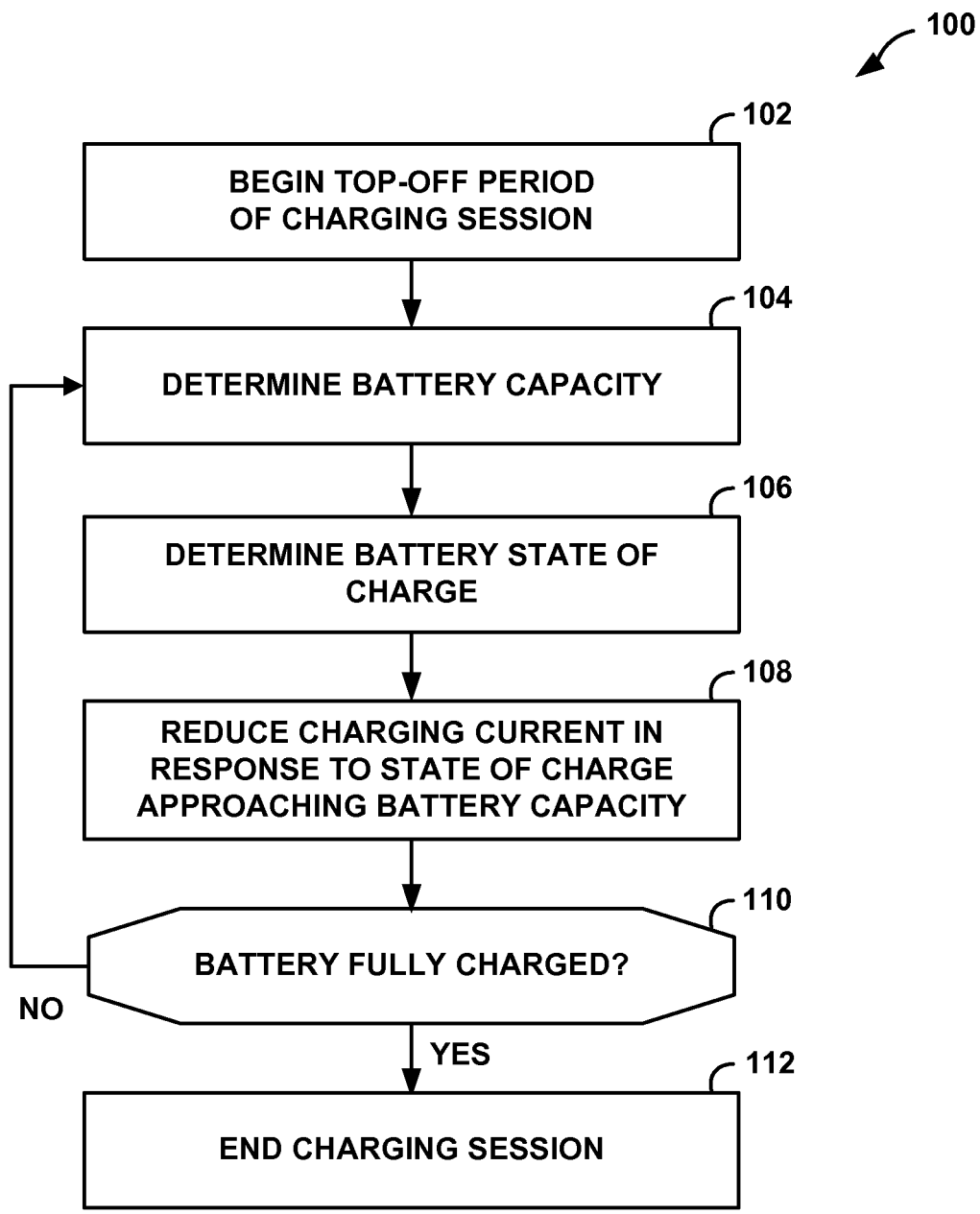
FIG. 7 is a flow chart illustrating an example method of recharging a battery according to aspects of this disclosure.

FIG. 7 is a flow chart illustrating an example method 100 of recharging a power source, according to aspects of this disclosure. Although generally described as being performed by components of IMD 34 (FIGS. 2, 3) and programmer 40 (FIGS. 2, 4) for purposes of explanation, it should be understood that other implantable stimulators, charging devices and programmers, such as implantable stimulator 4 and programmer 20 (FIG. 1), or a variety of other devices may also be configured to perform the charging session shown in FIG. 7. In addition, power source 56 is generally referred in the example method of FIG. 7 as a battery. As noted above, however, power source 56 may include one or more batteries, capacitors, supercapacitors, or any combination thereof.

IMD 34 begins a top-off period of a charging session (102). In some examples, as noted above, IMD 34 may begin the top-off period upon recharging the battery to a certain amount (e.g., a state of charge of the battery reaching a predetermined level). For example, IMD 34 may begin the top-off period upon the battery reaching 40% charged. In other examples, IMD 34 may begin the top-off period relatively later in the charging session, e.g., upon the battery reaching 80% charged. The point at which IMD 34 begins the top-off period may vary based on, for example, the configuration/capability of the battery, the age of the battery, the configuration/capability of programmer 40, or other factors.

During the top-off period, IMD 34 determines the battery capacity (104). In some examples, battery capacity for a current charging session may be estimated based on an amount of charge applied to the battery during a previous charging session. For example, coulomb counter 62 of IMD 34 may track an amount of charge that is expended by IMD 34, as well as an amount of charge that is stored by the battery during a charging session, assuming the battery is fully charged during each charging session. Accordingly, IMD 34 may estimate a new battery capacity after each charging session, based on the amount of charge that was expended versus the amount of charge that was applied during the charging session. In this way, IMD 34 may adjust the capacity of the battery as the battery degrades and is able to store relatively less charge.

IMD 34 also determines the battery state of charge (106). For example, IMD 34 may determine the battery state of charge relative to the battery capacity. In some examples, IMD 34 may use coulomb counter 62 to determine the state of charge. For example, given a certain battery capacity (e.g., an estimated battery capacity), IMD 34 may determine the state of charge of the battery as charge is applied to the battery relative to the calculated battery capacity.

In some examples, according to aspects of this disclosure, IMD 34 may reduce the charging current that is applied to the battery in response to the state of charge of the battery approaching the battery capacity (108). In some examples, as described with respect to FIG. 6 above, IMD 34 may reduce, or "step down" the charging current more than once during the top-off period. In other examples, IMD 34 may continually and gradually reduce the charging current during the top-off period. In any event, the charging current may be reduced such that a voltage of the battery is maintained below some predefined voltage limit.

IMD 34 then determines whether the battery is fully charged (110). In some examples, determining whether the battery is fully charged may include determining whether a minimum charging current of the top-off period has been reached. In other examples, determining whether the battery is fully charged may include determining whether a voltage limit has been reached. In other examples, determining whether the battery is fully charged may include counting a number of coulombs of charge (or measuring an amount of current) that has been applied to the battery during charging and determining whether the charge applied matches the battery capacity. In other examples, some combination of these methods may be used to determine whether the battery is charged (e.g., a minimum charging current is reached and a voltage limit is reached).

If IMD 34 determines that charging is complete (the "yes" branch of step 110), IMD 34 may end the charging session (112). In some examples, an indication may be provided to patient 6 or a clinician, e.g., via user interface 63. If IMD 34 determines that charging is not complete (the "no" branch of step 110), IMD 34 may continue determining battery capacity (104), determining state of charge (106), and reducing the charging current in response to the state of charge approaching the battery capacity (108).

In some examples, the method shown and described with respect to FIG. 7 may be carried out by IMD 34 (e.g., processor 50). However, in other examples, the method of FIG. 7 may be performed by programmer 40 (e.g., processor 64). That is, for example, programmer 40 may be responsible for applying the appropriate charging current during the top-off period. In other examples, certain steps and/or functions of the method shown in FIG. 7 may be performed by both IMD 34 and programmer 40 in combination.

It should also be understood that the steps shown and described with respect to FIG. 7 are provided as merely one example. That is, the steps of the method of FIG. 7 need not necessarily be performed in the order shown in FIG. 7, and fewer, additional, or alternative steps may be performed.

Figure 8:
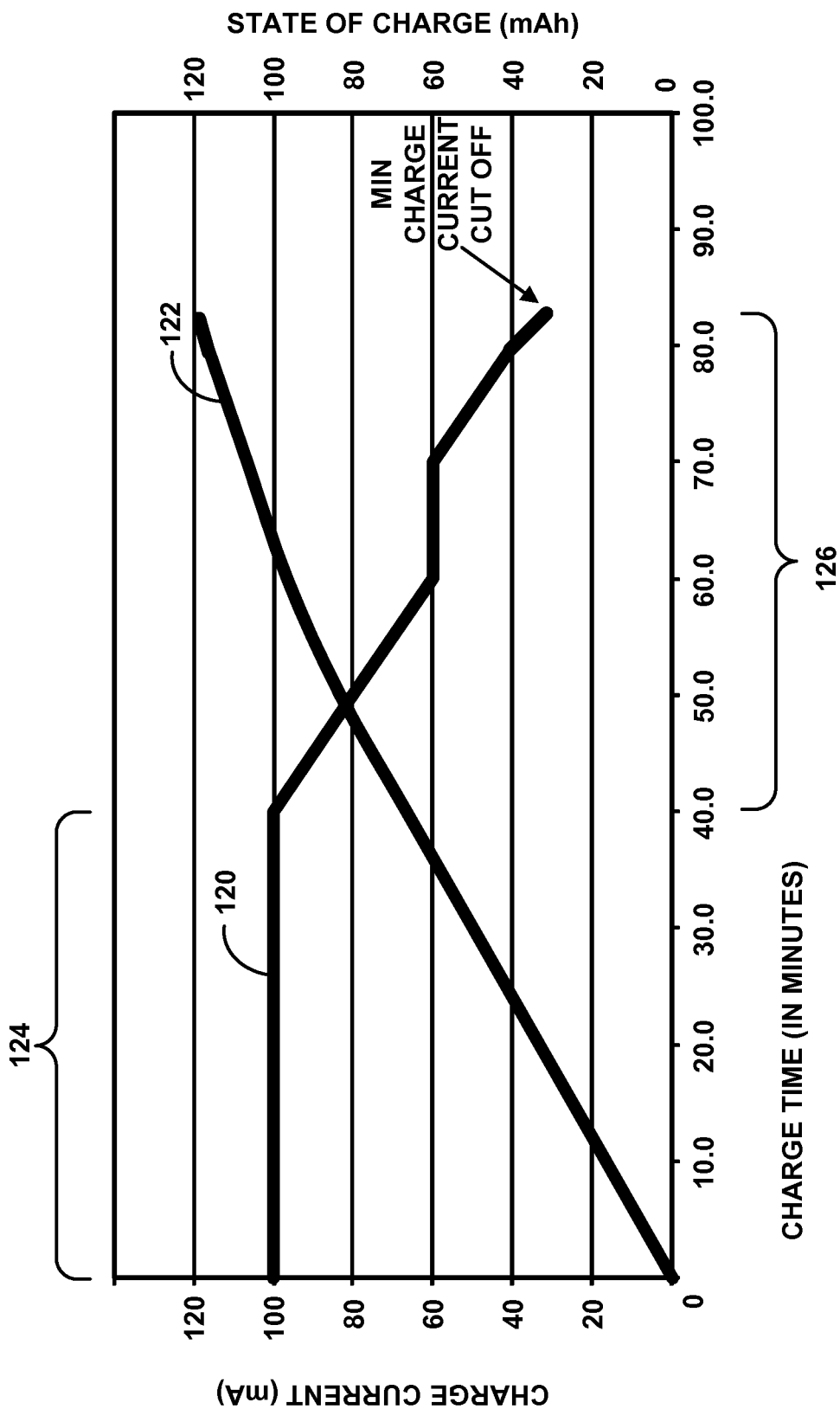
FIG. 8 is a graph illustrating an example charging session having a top-off period.

FIG. 8 is a graph illustrating an example charging session having a top-off period. Although generally described as being performed by components of IMD 34 (FIGS. 2, 3) and programmer 40 (FIGS. 2, 4) for purposes of explanation, it should be understood that other implantable stimulators and programmers, such as implantable stimulator 4 and programmer 20 (FIG. 1), or a variety of other devices may also be configured to perform the charging session shown in FIG. 8. Moreover, in other examples, IMD 34 and/or programmer 40 may perform different functions than those described with respect to FIG. 8 (e.g., IMD 34 may perform functions attributed to programmer 40, and vice versa).

The example graph shown in FIG. 8 tracks a charging current 120 and a state of charge 122 throughout a charging session of power source 56. The example shown in FIG. 8 may be a charging session for a relatively new 120 mAh power source 56. That is, the example shown in FIG. 8 may be associated with a newly manufactured and/or implanted IMD 34. In the example shown in FIG. 8, charging current 120 is measured in milliamps (mA) and state of charge 122 is measured in milliamp-hours (mAh). In other examples, state of charge 122 may also be represented as a percentage of the battery capacity (e.g., 50% of full charge).

Programmer 40 applies a charging current 120 to power source 56 during an initial charging period 124. During the initial charging period 124, programmer 40 may apply a maximum charging current to power source 56 in order to charge power source 56 as quickly as possible without damaging power source 56. In the example shown in FIG. 8, programmer 40 applies a maximum charging current of approximately 100 milliamps (mA) during the initial charging period 124. In other examples, the maximum charging current may vary depending on, for example, the capabilities of power source 56, the capabilities of programmer 40, or other factors.

In the example shown in FIG. 8, IMD 34 reduces a charging current 120 during top-off period 126. IMD 34 may reduce charging current 120 due to shunting (e.g., reaching a voltage limit, as described above) and/or in accordance with a predefined charging algorithm. In the example of FIG. 8, IMD 34 may continue to reduce charging current 120 during top-off period 126 until reaching a predetermined minimum charging current cut off ("MIN CHARGE CURRENT CUT OFF"). That is, IMD 34 may continue to charge power source 56 until a predefined, minimum charging current 120 is reached. The minimum charging current may be the smallest current at which IMD 34 is allowed to charge power source 56. For example, it may not be beneficial to charge power source 56 using a charging current that is lower than the minimum charging current, as power source 56 may not be effectively charged, the charging session may take too long, and the like.

The minimum charging current cut off may be initially set (e.g., at the time of manufacture or implantation) so that the minimum charging current cut off is reached at the same time that power source 56 reaches full charge. In the example shown in FIG. 8, power source 56 reaches a full charge (e.g., assuming a 120 mAh battery) at a minimum charging current cut off of approximately 30 mA. In addition, power source 56 reaches full charge after a charging session of approximately 80 and 85 minutes. The predefined minimum charging current cut off shown in FIG. 8 may not be adaptive to changing conditions of power source 56, as described in greater detail with respect to FIGS. 9-11 below.

Figure 9:
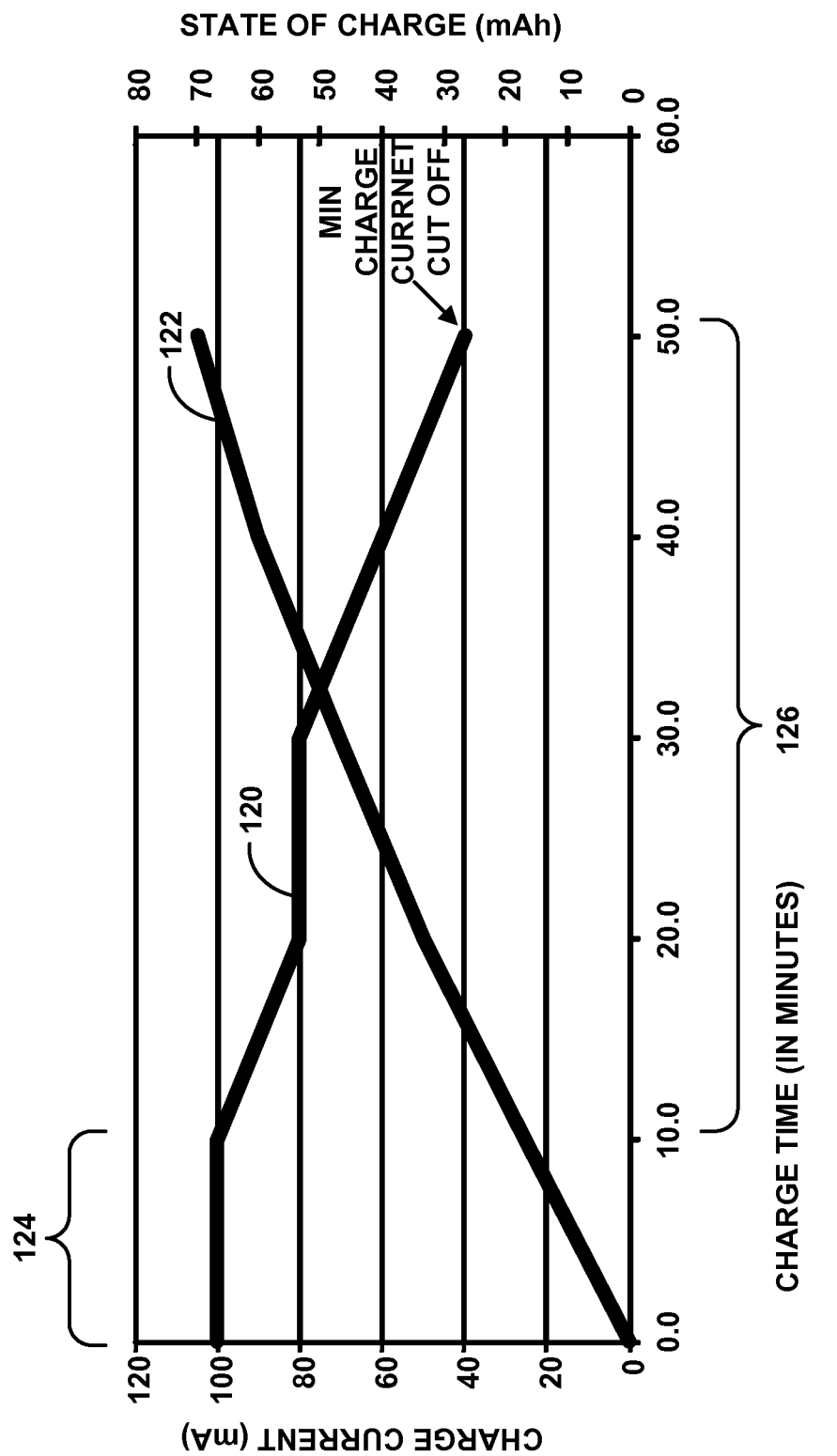
FIG. 9 is a graph illustrating another example charging session having another top-off period.

FIG. 9 is a graph illustrating an example charging session for power source 56 having the same predetermined minimum charging current cut off as that shown in FIG. 8 (e.g., approximately 30 mA). The example of FIG. 9, however, may represent a relatively older power source 56 that has higher impedance than that associated with FIG. 8. That is, in some examples, the impedance of power source 56 may increase over time. For example, the impedance of power source 56 may increase due to natural degradation of power source 56 (e.g., associated with discharging and charging cycles) and/or other wear or damage to power source 56.

The higher impedance of power source 56 may cause power source 56 to reach a voltage limit (e.g., due to IMD 34 shunting current) earlier in the charging session than the lower impedance power source 56. Accordingly, IMD 34 may reduce charging current 120 during top-off period 126 shown in FIG. 9 relatively sooner than the lower impedance power source 56 shown in FIG. 8. In addition, the minimum charging current cut off (e.g., 30 mA) is achieved in a relatively shorter amount of time. That is, where the example shown in FIG. 8 reaches the minimum charging current cut off in approximately 80 to 85 minutes, the example shown in FIG. 9 reaches the minimum charging current cut off in approximately 50 minutes. Accordingly, the state of charge 122 that is achieved in power source 56 having the higher impedance is less (FIG. 9) than that achieved in power source 56 having the lower impedance (FIG. 10). For example, the state of charge is approximately 70 mAh in FIG. 9 versus approximately 120 mAh in FIG. 8.

Figure 10:
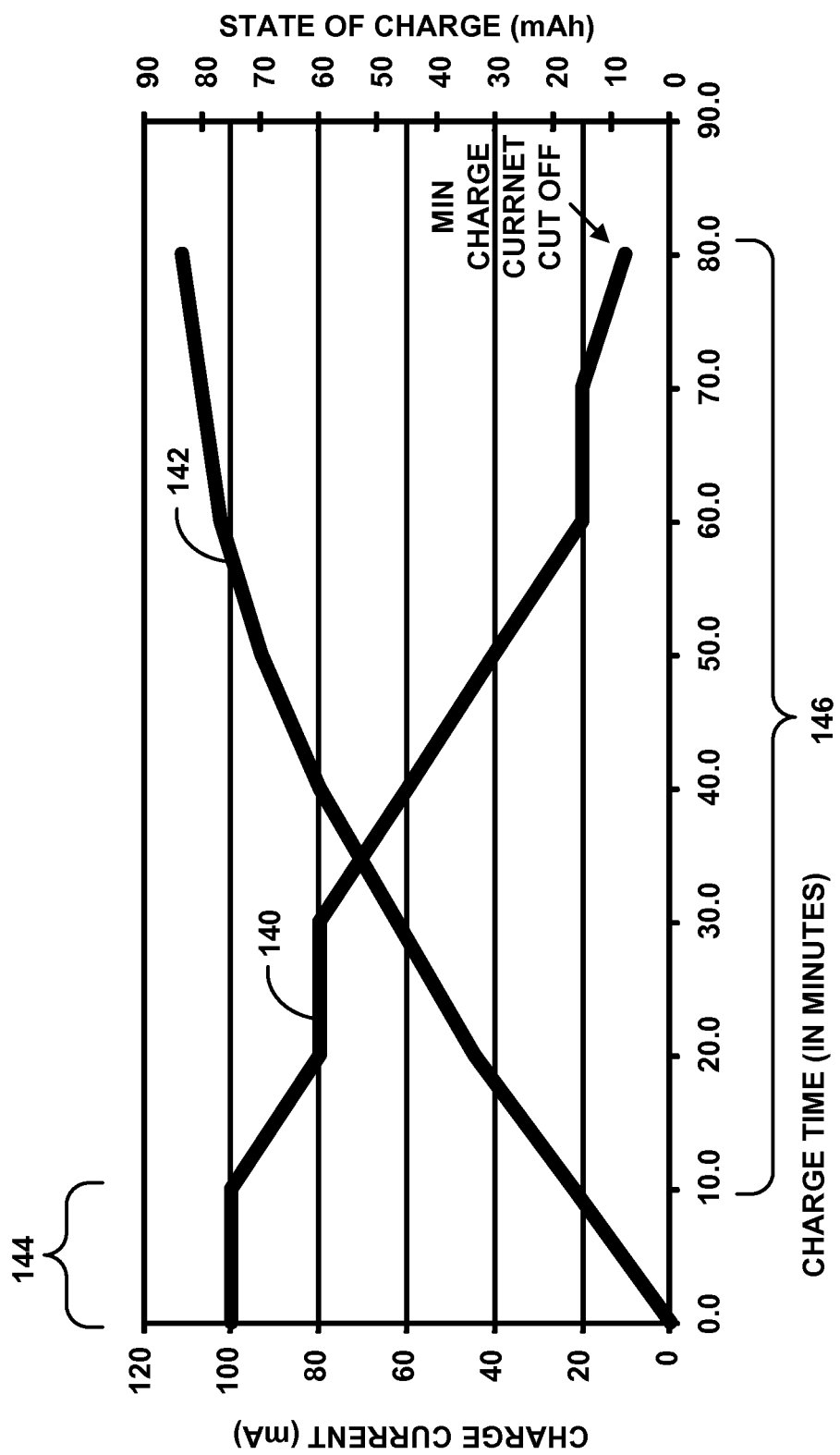
FIG. 10 is a graph illustrating another example charging session having another top-off period.

FIG. 10 is a graph illustrating an example charging session having a top-off period that includes a minimum charging current cut off, which may be adapted to account for changing battery conditions in accordance with the techniques of this disclosure. That is, the example charging session shown in FIG. 10 may be associated with the same high impedance power source 56 described with respect to FIG. 9. In the example of FIG. 10, however, the minimum charging current cut off has been adapted to account for the higher impedance, as described in greater detail below.

Although generally described as being performed by components of IMD 34 (FIGS. 2, 3) and programmer 40 (FIGS. 2, 4) for purposes of explanation, it should be understood that other implantable stimulators, charging devices and programmers, such as implantable stimulator 4 and programmer 20 (FIG. 1), or a variety of other devices may also be configured to perform the charging session shown in FIG. 10.

In the example of FIG. 10, programmer 40 applies a charging current 140 to power source 56 during an initial charging period 144. During the initial charging period 144, programmer 40 may apply a maximum charging current to power source 56 in order to charge power source 56 as quickly as possible without damaging power source 56. In the example shown in FIG. 10, programmer 20 applies a maximum charging current of approximately 100 milliamps (mA) during the initial charging period 144. In other examples, the maximum charging current may vary depending on, for example, the capabilities of power source 56, the capabilities of programmer 20, or other factors.

The graph shown in FIG. 10 may be associated with the same relatively high impedance power source associated with FIG. 9. That is, IMD 34 may reduce charging current 140 during top-off period 146. As shown in FIG. 10, however, implantable stimulator may reduce a minimum charge current cut off ("MIN CHARGE CURRENT CUT OFF") in accordance with the techniques of this disclosure.

For example, IMD 34 may initially determine a duration of a previous charging session, as well as an amount of charge that was administered to power source 56 during the previous charging session. IMD 34 may then, according to the techniques of this disclosure, determine the top-off charging current cut off based on the duration of the previous charging session. For example, IMD 34 may compare the duration of the previous charging session to a predefined target duration. If the duration of the previous charging session was shorter than the target duration (e.g., power source 56 completed charging in less time than the target duration), IMD 34 may allow power source 56 to be charged during top-off for a longer duration using a lower minimum charging current cut off. Alternatively, if the duration of the previous charging session was longer than the target duration, IMD 34 may increase the minimum charging current cut off.

Additionally or alternatively, according to aspects of this disclosure, IMD 34 may determine the top-off charging current cut off based on an amount of charge administered during the previous charging session. For example, if the amount of charge delivered during the previous charging session does not charge power source 56 to full or nearly full capacity, IMD 34 may lower the minimum charging current cut off. Lowering the minimum charging current cut off may increase the duration of the top-off period and allow more charge to be administered to power source 56.

In other examples, IMD 34 may implement a balancing approach that considers both the charge administered during the first charging session and the target duration. For example, IMD 34 may attempt to maximize an amount of charge administered to power source 56 while still maintaining the charging session to within a predetermined time range.

In the example shown in FIG. 10, IMD 34 lowers the minimum charging current cut off from approximately 40 mA (FIG. 9) to approximately 10 mA. As shown in the example of FIG. 10, reducing the minimum charging current cut off results in an increased charging duration, as well as an increase in the amount of charge that is administered to power source 56 during charging. For example, the charging session shown in FIG. 10 lasts for approximately 80 minutes while charging power source to approximately 80 to 90 mAh of charge. In contrast, the charging session shown in FIG. 9 lasts for only approximately 50 minutes while charging power source to approximately 70 mAh of charge.

Adapting the minimum charging current cut off for a current charging session based on how much charge was put into power source 56 during a previous charging session and a duration of the previous recharge session allows IMD 34 to maintain the current charging session to a predetermined (target) time, while also cutting off the current recharging session if the charging current being applied to power source 56 is lower than a certain amount.

While the examples shown in FIGS. 8-10 are described with respect to a minimum charging current cut off, it should be understood that, in other examples, other charging termination parameters may be used to end a charging session. For example, a power cut off value may be used to end a charging session. The power level cut off may be based on a power output of programmer 40 (or another charging device). Thus, programmer 40 may continue charging power source 56 until reaching the power level cut off, which may be a minimum power level that may be used to charge power source 56. In this example, according to the techniques of this disclosure, IMD 34 and/or programmer 40 may adapt the power level cut value off based on the duration of the previous charging session and/or an amount of charge administered during the previous charging session. In still other examples, other charging termination parameters may be used, such as other parameters that indicate when a battery has reached full charge.

Figure 11:
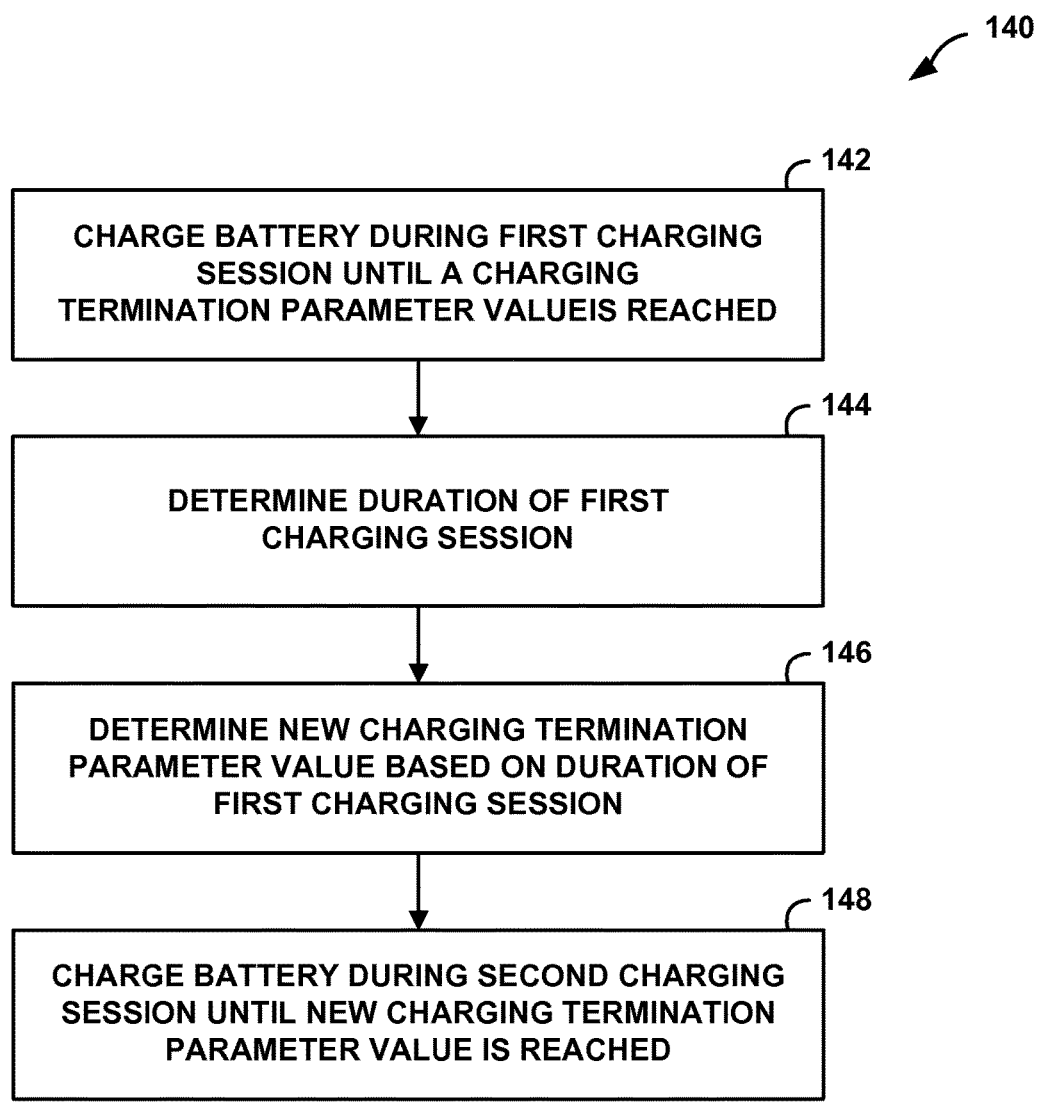
FIG. 11 is a flow chart illustrating an example method of recharging a battery according to aspects of this disclosure.

FIG. 11 is a flow chart illustrating an example method 140 of recharging a power source, according to aspects of this disclosure. Although generally described as being performed by components of IMD 34 (FIGS. 2, 3) and programmer 40 (FIGS. 2, 4) for purposes of explanation, it should be understood that other implantable stimulators and programmers, such as implantable stimulator 4 and programmer 20 (FIG. 1), or a variety of other devices may also be configured to perform the charging session shown in FIG. 11. In addition, power source 56 is generally referred in the example method of FIG. 11 as a battery. As noted above, however, power source 56 may include one or more batteries, capacitors, supercapacitors, or any combination thereof.

IMD 34 recharges the battery during a first charging session until reaching a predetermined charging termination parameter value (a parameter value that, when attained, causes IMD 34 and/or programmer 40 to terminate the charging session) (142). The charging termination parameter may include, for example, a minimum charging current cut off, a power level cut off, a state of charge of the battery, and the like. For example, given a certain battery capacity (e.g., power capacity), IMD 34 may recharge the battery until a device responsible for charging the battery (e.g., programmer 40) lowers to a power level that occurs when the battery is approximately charged to cull capacity. Other charging termination parameters are also possible. As described with respect to FIGS. 8-10, with respect to the minimum charging current cut off example, the minimum charging current cut off may initially be set to a predetermined value that allows the battery to be fully charged.

IMD 34 then determines the duration of the first charging session (144). The duration of the first charging session may be determined, for example, by timing the charging session with a timer that begins when a charge is first applied to the battery and ends upon reaching the charging current cut off (e.g., ending the charging session). In some examples, as described in greater detail below, IMD 34 may also determine an amount of charge administered to the battery during the first charging session. The amount of charge administered to the battery may be determined, for example, using coulomb counter 62. That is, coulomb counter 62 may track a number of coulombs administered to the battery during charging. In other examples, IMD 34 may determine an amount of current that is administered to the battery during charging using coulomb counter 62.

IMD 34 then determines a new charging termination parameter value for the next charging session based on the duration of the previous charging session (146). For example, according to aspects of this disclosure, IMD 34 may compare the duration of the previous charging session to a predefined, target duration. In some examples, the target recharging time may be static and may be programmed at the time of manufacture of IMD 34. In other examples, the target recharging time may be determined by patient 36 and/or clinician. In such examples, the target recharging time may be input via programmer 40. In an example, the predefined target duration may be approximately one hour, although longer or shorter durations may be used depending, for example, on the configuration/capability of the battery, the configuration/capability of programmer 40, or other factors. For example, a relatively smaller battery may be associated with a relatively shorter target charging duration.

According to aspects of this disclosure, if the duration of the previous charging session was shorter than the target duration (e.g., the battery finished charging in less time than the target duration), IMD 34 may alter the charging termination parameter value in a way that increases the duration of the next charging session. For example, in examples in which the charging termination parameter is a minimum charging current cut off, IMD 34 may reduce the minimum charging current cut off value. That is, for example, IMD 34 may allow the battery to be charged a longer duration using a lower minimum charging current cut off. Alternatively, if the duration of the previous charging session was longer than the target duration, IMD 34 may increase the minimum charging current cut off. Altering the charging termination parameter in this way may be used primarily in situations in which the battery is being charged to a full charge from a fully depleted state.

According to aspects of this disclosure, IMD 34 may also consider the capacity of the battery in situations in which the battery is not fully discharged before beginning a charging session when determining the new charging termination parameter value. In an example for purposes of illustration, a user may begin charging IMD 34 despite the battery having approximately 50% charge remaining. The charging session may last approximately 20 minutes to charge the battery to a full charge. Accordingly, IMD 34 may determine that the next charging session requires 40 minutes to charge the battery from fully discharged to fully charged. Given a target recharge time of one hour, IMD 34 may alter the charging termination parameter value for the next charging session in an effort to increase the charging time to one hour. That is, for example, IMD 34 may lower a minimum charging current cut off value to increase the duration of the next charging session.

Additionally or alternatively, according to some aspects of this disclosure, IMD 34 may also determine the new charging termination parameter value based on a comparison of the amount of charge administered to the battery for the previous charging session to a capacity of the battery. In some examples, the battery capacity may be a static, predetermined value. In other examples, the battery capacity may be estimated based on an amount of charge applied to the battery, as described above. If the amount of charge delivered during the previous charging session does not charge the battery to full or nearly full capacity, IMD 34 may alter the predetermined charging termination parameter value accordingly. For example, IMD 34 may lower a minimum charging current cut off. Lowering the minimum charging current cut off may increase the duration of the top-off period and allow more charge to be administered to the battery. For example, by lowering the minimum charging current cut off, the battery can be maintained below a voltage limit (e.g., a charging voltage limit) for a longer period of time, and additional charge can be administered to the battery.

In some examples, IMD 34 may implement a balancing approach that considers both the charge administered during the first charging session and the target duration. In an example for purposes of illustration, assume the battery has a 110 mAh capacity, a first charging session ends with a 100 mAh state of charge, a 40 mA minimum charging current cut off, and a charging duration of approximately 50 minutes (given a target of 60 minutes). For the next charging session, IMD 34 may adjust a charging termination parameter value (e.g., a minimum charging current cut off value, or a value of another charging termination parameter described above) until the one hour target duration is achieved. Achieving the target charging duration may result in a 95 mAh state of charge and a minimum charging current cut off of approximately 30 mA. In a subsequent charging session, IMD 34 may adjust the minimum charging current cut off to achieve the target charging duration, to achieve a full state of charge, or a balance of the two (e.g., a charging time from 50 to 70 minutes and a state of charge of 90 to 110 mAh).

In this way, IMD 34 can account for changing battery impedance, while also maintaining a target charging time. For example, as noted above, higher battery impedance may cause a battery to reach a voltage limit during charging more quickly (e.g., relative to a battery having lower impedance). In addition, higher battery impedance may cause the battery to reach the charging termination parameter value more quickly, resulting in less charge being administered to the battery. According to the techniques of this disclosure, the charging termination parameter value may be adjusted to account for changing impedance and allow the battery to charge for a longer duration, while also ensuring that the duration of the charging session is not extended beyond a target duration.

After determining the new charging termination parameter value (146), IMD 34 may charge the battery during the next charging session until the new charging termination parameter value is reached (148). In some examples, the method shown and described with respect to FIG. 11 may be carried out by IMD 34 (e.g., processor 50). However, as noted with respect to FIGS. 3 and 4 above, the method of FIG. 11 may also be performed by programmer 40 (e.g., processor 64). That is, for example, programmer 40 may be responsible for applying the appropriate charging termination parameter value. In other examples, certain steps and/or functions of the method shown in FIG. 11 may be performed by both IMD 34 and programmer 40 in combination.

It should also be understood that the steps shown and described with respect to FIG. 11 are provided as merely one example. That is, the steps of the method of FIG. 11 need not necessarily be performed in the order shown in FIG. 11, and fewer, additional, or alternative steps may be performed.

The techniques described in this disclosure, including those attributed to processors 50, 62, coulomb counter 62, or various constituent components, may be implemented, at least in part, in hardware, software, firmware or any combination thereof. For example, various aspects of the techniques may be implemented within one or more processors, e.g., processors 50, 62, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

In general, the techniques described in this disclosure can be applied to devices that are powered by one or more power sources such as batteries or capacitors. The techniques may be applied to medical devices such implantable medical devices configured to deliver neurostimulation or other electrical stimulation therapy via implanted electrode arrays, carried by leads or otherwise, located proximate to the spinal cord, pelvic nerves, peripheral nerves, the stomach or other gastrointestinal organs, or within the brain of a patient. The techniques described in this disclosure can be applied to medical devices that may not include electrodes to provide electrical stimulation. For examples, the techniques described in this disclosure can be applied to medical devices that provide medication in accordance with a delivery schedule. The techniques described in this disclosure may also be applied to medical devices that are external to the patient, as well as medical devices that used to program other medical devices. The techniques described in this disclosure may also be applied to non-medical devices such as laptop computers, gaming counsels, mobile phones, personal digital assistants (PDAs), and other such devices.

Many aspects of the disclosure have been described. Various modifications may be made without departing from the scope of the claims. These and other aspects are within the scope of the following claims.

The invention claimed is:

1. A method of charging a battery, the method comprising:
charging the battery during a first charging session until a first charging termination parameter value is reached, the first charging termination parameter value being a value other than time;
determining a duration of the first charging session;
determining, for a second charging session, a second charging termination parameter value based on the determined duration of the first charging session, wherein the second charging termination parameter value is different than the first charging termination parameter value, the second charging termination parameter value being a value other than time; and
charging the battery during the second charging session until the second charging termination parameter value is reached.

2. The method of claim 1, wherein the first charging termination parameter value and the second charging termination parameter value comprise a first minimum charging current cut off value and a second minimum charging current cut off value, respectively.

3. The method of claim 1, wherein the first charging termination parameter value and the second charging termination parameter value comprise a first power level cut off value associated with a charging device and a second power level cut off value associated with the charging device, respectively.

4. The method of claim 1, wherein determining the second charging termination parameter value based on the duration of the first charging session comprises comparing the duration of the first charging session to a predetermined target duration.

5. The method of claim 4, further comprising, when the duration of the first charging session is less than the predetermined duration, adjusting the second charging termination parameter value to increase the duration of the second charging session.

6. The method of claim 5, wherein adjusting the second charging termination parameter value comprises decreasing a minimum charging current cut off value.

7. The method of claim 4, further comprising, when the duration of the first charging session is greater than the predetermined duration, adjusting the second charging termination parameter value to decrease the duration of the second charging session.

8. The method of claim 7, wherein adjusting the second charging termination parameter value comprises increasing a minimum charging current cut off value.

9. The method of claim 4, wherein the predetermined duration is approximately one hour.

10. The method of claim 1, further comprising determining the second charging termination parameter value based on the duration of the first charging session and an amount of charge administered to the battery during the first charging session.

11. The method of claim 10, wherein determining the amount of charge administered to the battery during the first charging session comprises determining a number of coulombs administered to the battery during the first charging session.

12. The method of claim 10, wherein the amount of charge administered to the battery during the first charging session provides an indication of the impedance of the battery.

13. The method of claim 12, wherein determining the second charging termination parameter value comprises decreasing the second charging termination parameter value with respect to the first charging termination parameter value to account for an increase in the impedance of the battery.

14. The method of claim 12, wherein determining the second charging termination parameter value comprises increasing the second charging termination parameter value with respect to the first charging termination parameter value to account for a decrease in the impedance of the battery.

15. The method of claim 1, wherein charging the battery comprises a transcutaneous inductive transfer of charge to the battery.

16. The method of claim 1, wherein the battery resides in a medical device and charging the battery comprises charging the battery with a medical device charger.

17. An implantable medical device (IMD) comprising:
a battery configured to power the IMD; and
one or more processors configured to:
control charging of the battery during a first charging session until a first charging termination parameter value is reached, the first charging termination parameter value being a value other than time;
determine a duration of the first charging session;
determine, for a second charging session, a second charging termination parameter value based on the determined duration of the first charging session, wherein the second charging termination parameter value is different than the first charging termination parameter value, the second charging termination parameter value being a value other than time; and
control charging of the battery during the second charging session until the second charging termination parameter value is reached.

18. The IMD of claim 17, wherein the first charging termination parameter value and the second charging termination parameter value comprise a first minimum charging current cut off value and a second minimum charging current cut off value, respectively.

19. The IMB of claim 17, wherein the first charging termination parameter value and the second charging termination parameter value comprise a first power level cut off associated with a charging device and a second power level cut off associated with the charging device, respectively.

20. The IMD of claim 17, wherein to determine the second charging termination parameter value based on the duration of the first charging session, the one or more processors are configured to compare the duration of the first charging session to a predetermined target duration.

21. The IMD of claim 20, wherein the one or more processors are configured to, when the duration of the first charging session is less than the predetermined duration, adjust the second charging termination parameter value to increase the duration of the second charging session.

22. The IMD of claim 21, wherein to adjust the second charging termination parameter value, the one or more processors are configured to decrease a minimum charging current cut off value.

23. The IMD of claim 20, wherein the one or more processors are configured to, when the duration of the first charging session is greater than the predetermined duration, adjust the second charging termination parameter value to decrease the duration of the second charging session.

24. The IMD of claim 23, wherein to adjust the second charging termination parameter value, the one or more processors are configured to increase a minimum charging current cut off value.

25. The IMB of claim 20, wherein the predetermined duration is approximately one hour.

26. The IMD of claim 17, wherein the one or more processors are further configured to determine the second charging termination parameter value based on the duration of the first charging session and an amount of charge administered to the battery during the first charging session.

27. The IMD of claim 26, wherein the one or more processors are further configured to determine the amount of charge administered to the battery during the first charging session by determining a number of coulombs administered to the battery during the first charging session.

28. The IMB of claim 26, wherein the amount of charge administered to the battery during the first charging session provides an indication of the impedance of the battery.

29. The IMD of claim 28, wherein to determine the second charging termination parameter value, the one or more processors are configured to decrease the second charging termination parameter value with respect to the first charging termination parameter value to account for an increase in the impedance of the battery.

30. The IMD of claim 28, wherein to determine the second charging termination parameter value, the one or more processors are configured to increase the second charging termination parameter value with respect to the first charging termination parameter value to account for a decrease in the impedance of the battery.

31. The IMB of claim 17, further comprising a charging module configured to inductively transfer charge to the battery transcutaneously.

32. An implantable medical device (IMD) comprising:
means for charging a battery during a first charging session until a first charging termination parameter value is reached, the first charging termination parameter value being a value other than time;
means for determining a duration of the first charging session;
means for determining, for a second charging session, a second charging termination parameter value based on the determined duration of the first charging session, wherein the second charging termination parameter value is different than the first charging termination parameter value, the second charging termination parameter value being a value other than time; and
wherein the means for charging the battery charges the battery during the second charging session until the second charging termination parameter value is reached.

33. The IMD of claim 32, wherein the means for determining the second charging termination parameter value based on the duration of the first charging session comprises means for comparing the duration of the first charging session to a predetermined target duration.

34. The IMD of claim 33, wherein, when the duration of the first charging session is less than the predetermined duration, further comprising means for adjusting the second charging termination parameter value to increase the duration of the second charging session.

35. The IMD of claim 34, wherein the means for adjusting the second charging termination parameter value comprises means for decreasing a minimum charging current cut off value.

36. The IMD of claim 33, wherein, when the duration of the first charging session is greater than the predetermined duration, further comprising means for adjusting the second charging termination parameter value to decrease the duration of the second charging session.

37. The IMD of claim 36, wherein the means for adjusting the second charging termination parameter value comprises means for increasing a minimum charging current cut off value.

38. A system comprising:
an implantable medical device (IMD) comprising a battery configured to power the IMD; and
a charging control unit configured to charge the battery of the IMD, wherein to charge the battery, the charging control unit is configured to:
control charging of the battery during a first charging session until a first charging termination parameter value is reached, the first charging termination parameter value being a value other than time;
determine a duration of the first charging session;
determine, for a second charging session, a second charging termination parameter value based on the determined duration of the first charging session, wherein the second charging termination parameter value is different than the first charging termination parameter value, the second charging termination parameter value being a value other than time; and
control charging of the battery during the second charging session until the second charging termination parameter value is reached.

39. The system of claim 38, wherein the charging control unit is included in the IMD.

40. The system of claim 38, wherein the charging control unit is included in an external programmer that is configured to communicate with the IMD.

* * * * *